(12) United States Patent
Gottesman et al.

(10) Patent No.: US 11,983,099 B1
(45) Date of Patent: May 14, 2024

(54) GRAPHICAL INTERVENTION TEST DEVELOPMENT SYSTEM

(71) Applicant: Flatiron Health, Inc., New York, NY (US)

(72) Inventors: Adam Gottesman, New York, NY (US); Alex Deyle, New York, NY (US); Barry Leybovich, New York, NY (US); Filip Frahm, New York, NY (US); Forrest Xiao, Minneapolis, MN (US); Jessie Tseng, Brooklyn, NY (US); Lauren Sutton, Cary, NC (US); Maneet Kaur, Port Jefferson, NY (US); Neal Meropol, Brooklyn, NY (US); Trevor Royce, Chapel Hill, NC (US); Yihua Zhao, Bedford, NY (US)

(73) Assignee: Flatiron Health, Inc., New York, NY (US)

( * ) Notice: Subject to any disclaimer, the term of this patent is extended or adjusted under 35 U.S.C. 154(b) by 0 days.

(21) Appl. No.: 18/352,844

(22) Filed: Jul. 14, 2023

(51) Int. Cl.
*G06F 9/44* (2018.01)
*G06F 11/36* (2006.01)

(52) U.S. Cl.
CPC ...... *G06F 11/3684* (2013.01); *G06F 11/3688* (2013.01)

(58) Field of Classification Search
CPC .................. G06F 11/3684; G06F 11/3688
See application file for complete search history.

(56) References Cited

U.S. PATENT DOCUMENTS

2022/0215908 A1* 7/2022 Padmos ................ G16H 10/60
2022/0334958 A1* 10/2022 Ui ....................... G06F 11/3684

* cited by examiner

*Primary Examiner* — Chat C Do
*Assistant Examiner* — Lenin Paulino
(74) *Attorney, Agent, or Firm* — Wolf, Greenfield & Sacks, P.C.

(57) ABSTRACT

Described herein is a graphical intervention test development system. The graphical intervention test development system provides a graphical intervention test development environment that facilitates computer-based design of an intervention test. The graphical intervention test development environment provides a graphical user interface (GUI) and visualizations of various aspects of an intervention test therein. The graphical intervention test development environment further provides a control interface through which a user can manipulate control parameters that affect outcomes of the intervention test.

16 Claims, 32 Drawing Sheets

All Studies

Create New Study

| Study name | Last Updated |
|---|---|
| Study Name 1 | 05/20/2022 by User 1 |
| Study name 2 | 05/20/2022 by User 1 |
| Study name 3 | 05/20/2022 by User 1 |
| Study name 4 | 05/20/2022 by User 1 |
| Study name 5 | 05/20/2022 by User 1 |
| Study name 6 | 05/20/2022 by User 1 |
| Study name 7 | 05/20/2022 by User 1 |
| Study name 8 | 05/20/2022 by User 1 |
| Study name 9 | 05/20/2022 by User 1 |
| Study name 10 | 05/20/2022 by User 1 |

FIG. 4

Study X-1

User 1 | DLBCL

Analyses

| Analysis Name | Objective |
|---|---|
| No analyses saved. | |

Cohorts

| Cohort Name | EDM |
|---|---|
| DLBCL Baseline | DLBCL |

Add new cohort

Cohort name: [Cohort 1] — 710

Disease: [DLBCL ▼] — 712

Baseline: Patient included in database diagnosed with DCBL. At least two documented clinical visits, on different days, occurring on or after January 1, 2015

Inclusion / Exclusion Criteria

Refine selected disease cohort by including or excluding patients with certain characteristics.

- ● Include — 720a
- ○ Exclude — 722a

Diagnosis date ▼  between ▼  [Enter date] — 726  initial ▼ — 730  [Enter date] — 732
724 — 728  + Add date

- ○ Include — 720b
- ● Exclude — 722b

Therapy class ▼ — 734
Maintenance ▼ — 736
+ Add time

+ Add Criteria

[Save cohort]
[Cancel] — 738

View Dashboard

Request Custom Analysis

— 702

Patient Count: 1320 patients

[Add New Cohort]

User 1

STUDY X-1

User 1 | DLBCL

Analyses

| Analysis Name | Cohort | Analysis Type |
|---|---|---|
| Analysis 1 | Cohort 1 | Cohort Optimization |

Request Custom Analysis

Cohorts

| Cohort Name | EDM | Exclusion | Patient Count |
|---|---|---|---|
| Cohort 1 | DLBCL | — | 1320 patients |

Add New Cohort

View Dashboard

User 1

FIG. 20

Patterns of Care (2019)

| Characteristic | 1L | | | | | 2L | | | | |
|---|---|---|---|---|---|---|---|---|---|---|
| | Q1 N=206 | Q2 N=197 | Q3 N=198 | Q4 N=197 | Total N=798 | Q1 N=68 | Q2 N=59 | Q3 N=57 | Q4 N=60 | Total N=244 |
| Standard Therapy Class | | | | | | | | | | |
| Anti-CD19-based therapy | 0 (0%) | 0 (0%) | 0 (0%) | 0 (0%) | 0 (0%) | 0 (0%) | 0 (0%) | 0 (0%) | 0 (0%) | 0 (0%) |
| Anti-CD20-based monotherapy | 5 (2.4%) | 4 (2.0%) | 3 (1.5%) | 10 (5.1%) | 22 (2.8%) | 5 (7.4%) | 3 (5.1%) | 2 (3.5%) | 4 (6.7%) | 14 (5.7%) |
| Antibody-drug conjugate therapy | 0 (0%) | 0 (0%) | 0 (0%) | 0 (0%) | 0 (0%) | 0 (0%) | 0 (0%) | 4 (7.0%) | 2 (3.3%) | 6 (2.5%) |
| BTK inhibitor therapy | 2 (1.0%) | 0 (0%) | 0 (0%) | 2 (1.0%) | 4 (0.5%) | 2 (2.9%) | 1 (1.7%) | 4 (7.0%) | 0 (0%) | 7 (2.9%) |

FIG. 22

STUDY-135

Analysis Type
[ Cohort Optimization ▾ ]

Cohort
[ Cohort 1 ▾ ]  [ Edit ]

Includes:
- ECOG: Grade 0-1
- Bilirubin: 0
- Lymphocytes: 500+
- Hemoglobin: 10+
- Neutrophils: 1,500+
- Criteria B: 100
- Creatinine: 100

Cohort Optimization

Edit eligibility criteria impacting: [ Black Representativeness ▾ ]

| | | |
|---|---|---|
| Total Patients (Cohort 1) | 10,001 | |
| ECOG | 8,300 → 9,193 (+10%) | ⊙ Update |
| Suggested change: 0-2 to 0-3. | | |
| Bilirubin | 8,100 → 8,198 (+2%) | ⊙ Update |
| Suggested bilirubin range: 0-1 | | |

ECOG

Including patients with ECOG performance status grade of patient population by 127 and has little impact on Survival. more information.

| | All patients | Black patients |
|---|---|---|
| ☐ Already Included: ECOG Score 0-2 | 8,300 patients | 241 patients |

Line of therapy 1
Suggested:
9% of all possible patients
839 patients

[ Save Analysis ]

Demographics  Survival  Enrollment Projections  Site Selection

| Variable | Cohort 1: 10,001 | Trial Eligible Cohort 1: 7,000 | New Trial Eligible Cohort 1: 8,020 |
|---|---|---|---|
| ∨ Baseline + Diversity Characteristics | | | |
| Age (years) | 68.0 [58.5, 76.0] | 68.0 [58.0, 76.0] | 68.0 [58.0, 76.0] |

FIG. 23

| Factor | US Cancer Population | Data Population | Trial Population | Data Representativeness Score (1-10) | Trial Representativeness Score (1-10) |
|---|---|---|---|---|---|
| A | 5% | 7% | 1% | 1 | 7 |
| B | 40% | 45% | 10% | 2 | 9 |
| C | 90% | 84% | 40% | 3 | 9 |

FIG. 28

| Site name | Metric 1 | Metric 2 | Weighted Score |
|---|---|---|---|
| A | 1 | 4 | 1 |
| B | 5 | 10 | 2 |
| C | 8 | 8 | 3 |

FIG. 29

GRAPHICAL INTERVENTION TEST DEVELOPMENT SYSTEM

FIELD

Described herein is a graphical intervention test development system that provides a graphical intervention test development environment that facilitates computer-based design of intervention tests.

BACKGROUND

Intervention tests may be designed to test the efficacy of an intervention (e.g., medical procedure, pharmaceutical, and/or medical device). An intervention test may be conducted at various test sites (e.g., physician's offices, hospitals, academic institutions, etc.). Subjects at the various test sites may participate in the intervention test. Design of an intervention test may be overseen by a sponsor (e.g., a clinical trial sponsor). For example, sponsors may include, but are not limited to, government agencies, private individuals, companies or organizations, pharmaceutical companies, biotechnology companies, medical companies, and/or health care institutions. In some cases, a sponsor may contract a research organization (e.g., a clinical research organization (CRO)) to carry out an intervention test.

SUMMARY

Described herein is a graphical intervention test development system. The graphical intervention test development system provides a graphical intervention test development environment that facilitates computer-based design of an intervention test. The graphical intervention test development environment provides a graphical user interface (GUI) and visualizations of various aspects of an intervention test therein. The graphical intervention test development environment further provides a control interface through which a user can manipulate control parameters that affect outcomes of the intervention test.

Some embodiments provide a graphical intervention test development system. The system comprises: a processor; and a non-transitory computer-readable storage medium storing instructions that, when executed by the processor, cause the processor to execute a plurality of components of the graphical intervention development system. The plurality of components comprises: an intervention data module communicatively coupled to a database storing data about potential test points as values of fields, the intervention data module configured to: access a set of control parameters associated with an intervention test, the set of control parameters indicating a set of conditions for inclusion in the intervention test; access, from the database, data about a set of test points that meet the set of conditions indicated by the set of control parameters; and for each condition of the set of conditions, determine, using the data about the set of test points, a number of the set of test points that meet the condition; a graphical processing module configured to generate a graphical intervention test development environment, the graphical intervention test development environment comprising a graphical user interface (GUI), the graphical processing module configured to: receive, through the GUI, input indicating selection of the set of test points and selection of first control processing to be performed using the data about the set of test points; and an intervention test control module configured to: execute the first control processing using the data about the set of test points, wherein execution of the first control processing using the data causes the graphical processing module to render, in the GUI, a first visualization of the intervention test, the first visualization comprising: a plurality of graphical elements each representing a respective one of at least some the set of conditions and indicating a determined number of the set of test points that meet the condition; receive, through the GUI, input indicating an output measure of the intervention test; and identify one or more of the set of control parameters that impact the output measure of the intervention test; wherein the graphical processing module is further configured to update the first visualization by including, in the first visualization, a control interface configured to allow user modification of the one or more control parameters that impact the output measure.

Some embodiments provide a method of providing a graphical intervention test development environment for use in computer-based design of an intervention test. The method comprises using a processor to perform: accessing a set of control parameters associated with the intervention test, the set of control parameters indicating a set of conditions for inclusion in the intervention test; accessing, from a database storing data about potential test points as values of fields, data about a set of test points that meet the set of conditions indicated by the set of control parameters; determining, for each condition of the set of conditions, using the data about the set of test points, a number of the set of test points that meet the condition; generating the graphical intervention test development environment, the graphical intervention test development environment comprising a GUI; receiving, through the GUI, input indicating selection of the set of test points and selection of first control processing to be performed using the data about the set of test points; executing the first control processing using the data about the set of test points; rendering, in response to execution of the first control processing, a first visualization of the intervention test, the first visualization comprising: a plurality of graphical elements each representing a respective one of at least some of the set of conditions and indicating a determined number of the set of test points that meet the condition; receiving, through the GUI, input indicating an output measure of the intervention test; identifying one or more of the set of control parameters that impact the output measure of the intervention test; and updating the first visualization by including, in the first visualization, a control interface configured to allow user modification of the one or more control parameters that impact the output measure.

Some embodiments provide a non-transitory computer-readable storage medium storing instructions. The instructions, when executed by a processor, cause the processor to perform a method of providing a graphical intervention test development environment for use in computer-based design of an intervention test. The method comprises: accessing a set of control parameters associated with the intervention test, the set of control parameters indicating a set of conditions for inclusion in the intervention test; accessing, from a database storing data about potential test points as values of fields, data about a set of test points that meet the set of conditions indicated by the set of control parameters; determining, for each condition of the set of conditions, using the data about the set of test points, a number of the set of test points that meet the condition; generating the graphical intervention test development environment, the graphical intervention test development environment comprising a GUI; receiving, through the GUI, input indicating selection of the set of test points and selection of first control processing to be performed using the data about the set of test points; executing the first control processing using the data about the set of test points; rendering, in response to execution of the first control processing, a first visualization of the intervention test, the first visualization comprising: a plurality of graphical elements each representing a respective one of at least some of the set of conditions and indicating a determined number of the set of test points that meet the condition; receiving, through the GUI, input indicating an output measure of the intervention test; identifying one or more of the set of control parameters that impact the output measure of the intervention test; and updating the first visualization by including, in the first visualization, a control interface configured to allow user modification of the one or more control parameters that impact the output measure.

The foregoing is a non-limiting summary.

BRIEF DESCRIPTION OF DRAWINGS

Various aspects and embodiments will be described with reference to the following figures. It should be appreciated that the figures are not necessarily drawn to scale. Items appearing in multiple figures are indicated by the same or a similar reference number in all the figures in which they appear.

FIG. 4 is an illustrative graphical user interface (GUI) for accessing intervention tests in a graphical intervention test development system, according to some embodiments of the technology described herein.

FIG. 7 is an illustrative GUI through which a user may specify control parameters to generate a set of test points for an intervention test, according to some embodiments of the technology described herein.

FIG. 10 is an illustrative GUI through which a user may modify one or more control parameters to change a set of test points, according to some embodiments of the technology described herein.

FIG. 13 shows configuration options that can be used to modify the visualization of intervention test sites displayed in the GUI of FIG. 12, according to some embodiments of the technology described herein.

FIG. 20 is an illustrative GUI showing an intervention test updated to show results of control processing on data about a set of test points, according to some embodiments of the technology described herein.

FIG. 22 is an example of a table that describes a distribution of interventions over a given time period, according to some embodiments of the technology described herein.

FIG. 23 is an illustrative GUI showing manipulation of a GUI element to modify a control parameter controlling a condition for inclusion of test points in an intervention test, according to some embodiments of the technology described herein.

FIG. 28 shows an example visualization of representativeness of a set of test points, according to some embodiments of the technology described herein.

FIG. 29 shows an example visualization of metrics for various intervention sites, according to some embodiments of the technology described herein.

DETAILED DESCRIPTION

Figure 1A:
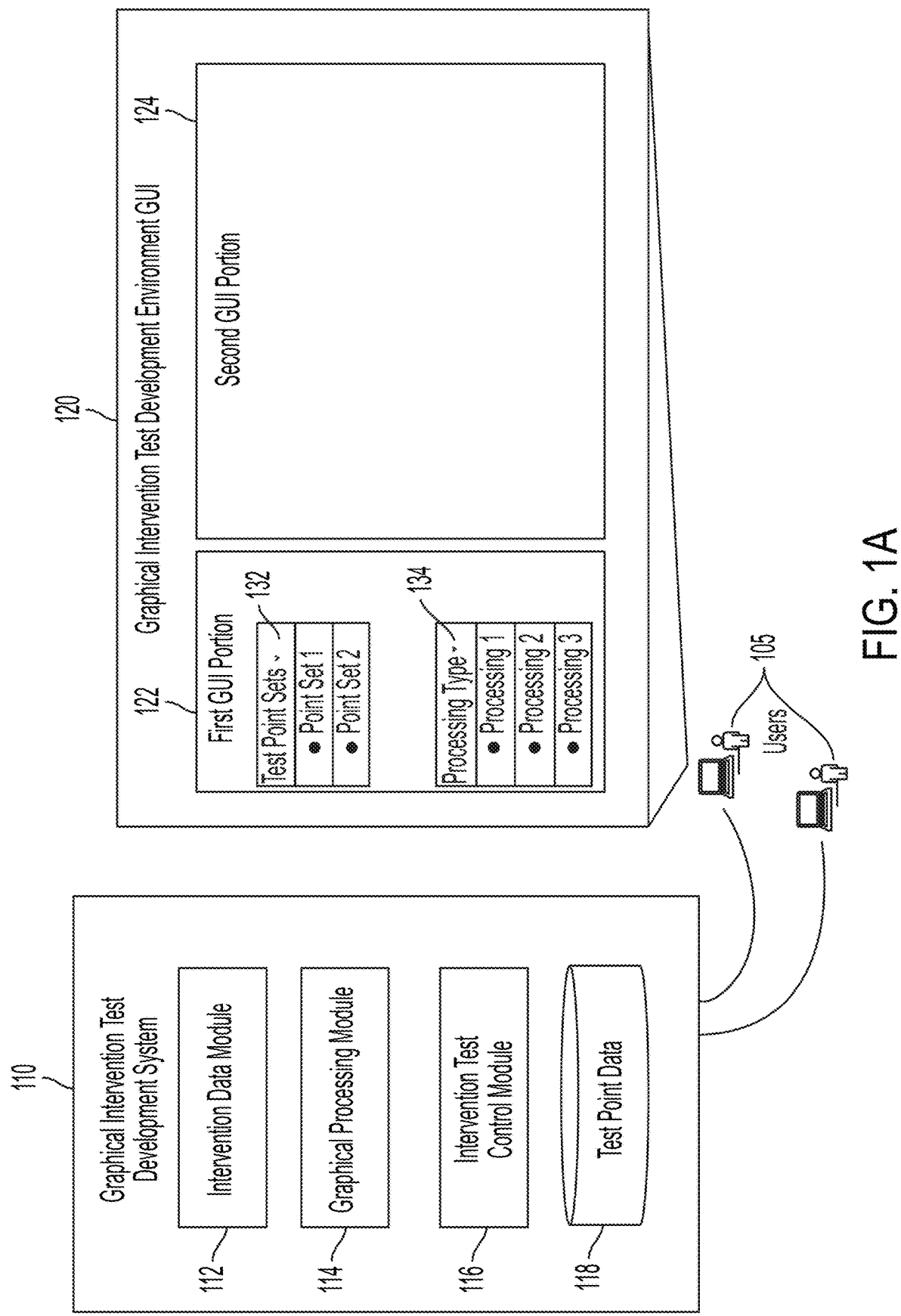
FIG. 1A is a diagram of an illustrative graphical intervention test development system, according to some embodiments of the technology described herein.

Described herein is a graphical intervention test development system that provides a graphical intervention test development environment for designing an intervention test. The graphical intervention test development environment includes a graphical user interface (GUI) in which the system renders visualizations of various aspects of an intervention test. The graphical intervention test development environment further includes a control interface through which control parameters of the intervention test can be manipulated to control aspects of the intervention test. The system may dynamically update visualizations in the GUI in response to manipulation of control parameters to provide a visualization of effects of the modifications.

An intervention test may be designed to test the efficacy of an intervention in subjects. For example, an intervention test may be a clinical trial or clinical study designed to test the efficacy of a medical procedure, medical treatment, medical device, pharmaceutical, drug, or other type of intervention. Designing an intervention test involves determining several parameters that control the execution of the intervention test. For example, control parameters may dictate conditions for the inclusion of test points in an intervention test, sites at which the intervention test is executed, and/or other aspects of the intervention test. A test point may refer to a candidate (e.g., a patient, subject, or other type of candidate) that may be included in an intervention test. Given how frequently new interventions are developed, there is a frequent need to develop intervention tests to test the efficacy of the interventions. Developing an intervention test to test the efficacy of an intervention is a complex process that requires the configuration of a large number of control parameters that define the intervention test. Moreover, modifications in a control parameter may significantly impact the result and usefulness of an intervention test.

One aspect of an intervention test that is dictated by control parameters of the intervention test is the accurate representativeness of a population by a set of test points included in the intervention test. Control parameters may specify a set of conditions for the inclusion of test points in the intervention test. If the set of conditions is poorly selected, the test points included in the intervention test may not adequately represent the population. This negatively impacts the quality of results obtained from the execution of the intervention test and, as a result, may negatively impact the use of the intervention test results. Another aspect of an intervention test that is dictated by control parameters of an intervention test is the set of sites (e.g., geographic regions) in which the intervention test is to be executed. Improper selection of sites may lead to intervention results that do not accurately reflect the efficacy of an intervention on a population.

Conventional intervention test development techniques fail to efficiently develop intervention tests that effectively test the efficacy of interventions. Conventional techniques develop new intervention tests by allowing a user to recycle parameters from previously developed intervention tests. This approach, however, introduces biases associated with previous intervention tests which may negatively impact the new intervention test being developed. For example, control parameters from a previous intervention test may specify a set of conditions that exclude certain test points from an intervention test that would otherwise be included. Further, conventional techniques do not provide a mechanism to restrict or preclude the user from configuring parameters in a manner that negatively impacts the intervention test (e.g., by worsening the representativeness of a population provided by test points, including test points whose health is at risk by participating in the intervention test, and/or selecting intervention test sites that poorly represent a population). Instead, conventional techniques rely on a user's expert knowledge and/or the user's ability to account for dynamic variables that affect the intervention test (e.g., guidelines set forth by the U.S. Food and Drug Administration (FDA)).

Accordingly, the inventors have developed a graphical intervention test development system to address the above-described shortcomings in conventional intervention test development techniques. The system provides a graphical intervention test development environment that generates visualizations of aspects of an intervention test, allows a user to configure control parameters for the intervention test, and generates visualizations of the effects of control parameter modifications on the intervention test. The system accesses data that conventional intervention test development techniques are unable to, and uses the data to: (1) generate visualizations of an intervention test; (2) determine effects of control parameter configurations on the intervention test; and (3) generate visualizations of the effects. The graphical environment includes a GUI that allows a user to configure control parameters of an intervention test, view the effects of control parameter configuration on aspects of an intervention test (e.g., test point inclusion, site selection, representativeness of test points included in the intervention test, survival or test points, patterns of intervention, and/or other aspects), and assess impacts of the configuration on the intervention test (e.g., on one or more output measures).

In some embodiments, the graphical intervention test development system may incorporate real-world data (RWD) in determining the effects of control parameters associated with an intervention test and generating visualizations illustrating those effects. For example, RWD may include clinical record data associated with test points. The clinical record data may include information about health (e.g., diagnoses illness, stage of illness, age, weight, height, allergies, comorbidities, date of birth, and/or other information), information about social determinants of health (SDoH) (e.g., employment, income, expenses, debt, medical bills, support, geography, housing, transportation, hunger, discrimination, stress, health cover, and/or other SDoH), and intervention information (e.g., prescribed drugs, medical test history, medical image data, and/or other information). RWD may be accessed by the system from various different data sources (e.g., through application program interfaces (APIs) associated with the datastores). For example, the system may access RWD by querying an electronic health record (EHR) database, querying an insurance claims database, accessing data from a health monitoring device, accessing information from a wearable device, accessing data from a mobile device, and/or other data sources. The graphical intervention test development system integrates the data about test points with control parameter configurations to generate graphical visualizations that facilitate the development of an intervention test.

The graphical intervention test development system may allow efficient design of an intervention test by leveraging real-world data (RWD) through the use of highly intuitive GUIs. These GUIs graphically depict aspects of an intervention test that conventional intervention test development systems are unable to. The GUIs reduce instances where suboptimal control parameters are used for an intervention test. The system further eliminates the need to execute various operations in developing an intervention test design. For example, the system eliminates the need to access multiple different web pages, execute multiple different application programs, execute queries on disparate databases, and/or execute other operations which would otherwise place an additional burden on computing resources of an intervention test development system.

The system further improves intervention test design technology because it allows users, such as clinical trial personnel, to assess the impact of eligibility criteria on intervention test design to reduce instances where suboptimal eligibility criteria (or other criteria) may be defined for the clinical trial. The techniques developed by the inventors include: (1) techniques for identification of eligibility criteria impacting a desirable output of the intervention test; (2) techniques for informing intervention site selection; and (3) GUIs to provide intuitive visualizations of aspects of intervention test design including manipulation of eligibility criteria using system-suggested changes to assess how the manipulation impacts an output measure for the intervention test. The GUIs can assist clinical trial personnel to assess various aspects of intervention test design, such as eligibility criteria, cohort size, cohort representativeness, site selection, cohort real-world overall survival, cohort patterns of care, and/or other aspects. For example, the system may generate visualizations of representation of a particular racial/ethnic group and/or visualizations of socioeconomic representations, provide a control interface to modify parameters that affect the representation(s) and update the visualizations to illustrate the effects of parameter modifications to the representativeness. Some embodiments of techniques described herein may improve intervention test participation for various groups (e.g., ethnic/racial groups and/or individuals of low socioeconomic status) and thus representativeness of those groups in intervention test results. For example, the techniques may allow identification of intervention test sites and control parameter modifications that improve representativeness of a group.

Some embodiments of techniques described herein provide a graphical intervention test development environment for use in computer-based design of an intervention test. The techniques: (1) access a set of control parameters associated with the intervention test, the set of control parameters indicating a set of conditions (e.g., threshold estimated glomerular filtration rate (eGFR) rate, Eastern Cooperative Oncology Group (ECOG) performance status range, bilirubin range, lymphocytes range, hemoglobin range, neutrophilis range, condition on socioeconomic variable(s), and/or other condition(s)) for inclusion in the intervention test; accessing, from a database storing data about potential test points as values of fields, data about a set of test points that meet the set of conditions indicated by the set of control parameters; (2) determine, for each condition of the set of conditions, using the data about the set of test points, a number of the set of test points that meet the condition; generating the graphical intervention test development environment, the graphical intervention test development environment comprising a GUI; (3) receive, through the GUI, input indicating selection of the set of test points and selection of first control processing to be performed using the data about the set of test points; (4) execute the first control processing using the data about the set of test points; and (5) render, in response to execution of the first control processing, a first visualization of the intervention test. The first visualization comprises a plurality of graphical elements each representing a respective one of at least some of the set of conditions and indicating a determined number of the set of test points that meet the condition. The techniques: (1) receive, through the GUI, input indicating an output measure (e.g., black representativeness, low socioeconomic status representativeness, Hispanic/Latin count, absolute test point count, survival, and/or other output measure) of the intervention test; (2) identify one or more of the set of control parameters that impact the output measure of the intervention test; and (3) update the first visualization by including, in the first visualization, a control interface configured to allow user modification of the one or more control parameters that impact the output measure.

In some embodiments, the techniques: (1) determine an impact (e.g., an increase or decrease in number of test points included in the intervention test) of a modification to the one or more control parameters to a number of test points that would meet the set of conditions after the modification; and (2) include, in the first visualization, a graphical indication of the determined impact of the modification to the one or more control parameters to the number of test points that would meet the set of conditions after the modification. In some embodiments, the techniques receive, through the control interface, input indicating a first modification to a first control parameter of the one or more control parameters that changes the set of conditions for inclusion in the intervention test. In some embodiments, the techniques determine an updated set of test points that meet the updated set of conditions in response to the first modification to the first control parameter to obtain an updated set of test points. In some embodiments, the techniques render, in the GUI, a second visualization of the intervention test using data about the updated set of test points.

In some embodiments, the techniques generate, in the GUI, a GUI portion configured to receive input indicating the set of control parameters. In some embodiments, the set of control parameters include at least one control parameter indicating a disease shared by the set of test points.

In some embodiments, the techniques may: (1) receive, through the GUI, input indicating selection of second control processing to be performed using the data about the set of test points, the second control processing comprising determining patterns of intervention for the set of test points; (2) execute the second control processing using the data; and (3) render, in the GUI in response to executing the second control processing, a second visualization indicating the patterns of intervention for the set of test points.

In some embodiments, the techniques may: (1) receive, through the GUI, input indicating selection of second control processing to be performed using the data about the set of test points, the second control processing comprising determining survival associated with the set of test points; (2) execute the second control processing using the data; and (3) render, in the GUI in response to executing the second control processing, a second visualization indicating the survival associated with the set test points.

In some embodiments, the first visualization may include a visualization of one or more socioeconomic variables for test points included in the intervention test. For example, the first visualization may include a visualization of household income for test points included in the intervention test. In some embodiments, the set of conditions may include one or more conditions on a socioeconomic variable. For example, the set of conditions may include a condition on area socioeconomic status (SES) index for inclusion in the intervention test.

FIG. 1A is a diagram of an illustrative graphical intervention test development system 110, according to some embodiments of the technology described herein. Graphical intervention test development system 110 includes an intervention data module 112, a graphical processing module 114, an intervention test control module 116, and a datastore 118. Multiple users (e.g., individuals affiliated with sponsors of an intervention test or otherwise associated with the intervention test, such as intervention test personnel) may interact with the graphical intervention test development system 110 via respective computing devices 105.

Each of computing devices 105 may be any suitable type of electronic device which a user may use to interact with the graphical intervention test development system 110. In some embodiments, one or more of computing devices 105 may be a portable device such as a mobile smart phone, a personal digital assistant (PDA), a laptop computer, a tablet computer, or any other portable device that may be used to interact with the graphical intervention test development system 110. In some embodiments, one or more of computing devices 105 may be a fixed electronic device such as a desktop computer, a rack-mounted computer, or any other suitable fixed electronic device that may be used to interact with the graphical intervention test development system 110. In some embodiments, computing devices 105 may communicate with the graphical intervention test development system 110 via a communication network (such as a local area network, a wide area network, a corporate intranet, the Internet, and/or any other suitable network) using wired, wireless, and/or any other suitable type of connections, as aspects of the disclosure provided herein are not limited in this respect.

In some embodiments, a user may interact with the graphical intervention test development system 110 via any suitable application program configured to execute on the user's computing device 105. For example, the user may interact with the graphical intervention test development system 110 by using a web-browser application program. As another example, the user may interact with the graphical intervention test development system 110 by using a stand-alone application program dedicated to providing access to the graphical intervention test development system 110.

In some embodiments, a user may interact with the graphical intervention test development system 110 by interacting with various GUIs described herein that are generated by the graphical intervention test development system 110 and presented to the user via a display of the user's computing device 105.

In some embodiments, the graphical intervention test development system 110 may comprise one or more computing devices (e.g., servers, rack-mounted computer(s), desktop computer(s), etc.) each comprising one or more processors. The one or more computing devices forming the graphical intervention test development system 110 may be local, distributed (e.g., cloud), and may be connected via any suitable means. Graphical intervention test development system 110 may comprise one or more non-transitory computer-readable storage media (e.g., memory and/or one or more other non-volatile storage media) configured to store processor-executable instructions, that when executed by one or more processors of graphical intervention test development system 110, cause the graphical intervention test development system 110 to perform any of numerous functions described herein in relation to FIGS. 2-30.

In some embodiments, the graphical intervention test development system 110 may be configured to access clinical data records of test points that may potentially be included in an intervention test. The graphical intervention test development system 110 may be configured to communicate with one or more external systems to access the clinical data records. In some embodiments, the graphical intervention test development system 110 may access the clinical data records from one or more electronic health record (EHR) systems. For example, the graphical intervention test development system 110 may access medical notes and/or other records from an EHR system. In some embodiments, the graphical intervention test development system 100 may access the clinical data records from one or more databases that store information from EHR system(s). In some embodiments, clinical record data may be accessed from various different sources including insurance billing and claims, product registries, disease registries, lab records, test point-gathered data, monitoring devices (e.g., wearable devices and biometric monitoring devices), mobile devices, and/or other sources.

In some embodiments, the graphical intervention test development system 100 may access SDoH data. The graphical intervention test development system 100 may use the SDoH data in determining and/or depicting socioeconomic representation of an intervention test. For example, the graphical intervention test development system 100 may access SDoH data from an EHR, patient-reported data (e.g., an SDoH questionnaire), credit data, consumer data, provider information and site-level information (e.g., patient-provider racial/ethnic concordance, disproportionately serving people of color, distance to clinic), area-level information (e.g., zip code, neighborhood, city, state, county, and/or other area-level information), and/or other sources of SDoH data. Example SDoH data for an intervention test that the system 100 may access may include socioeconomic variables such as the following:

a. An area-level SES index variable and/or a variable indicating structural racism.
b. Household income
c. County, zip code tabulated area (ZCTA), or tract
d. Air quality indicator
e. Walkability index
f. Average distance from grocery store by race/ethnicity
g. Indication of whether an individual lives alone
h. Indication of whether an individual is in a single-parent household
i. Distance to nearest clinic, emergency department (ED), intensive care unit (ICU), trauma center, or obstetrics department
j. Indicator of racial segregation (e.g., dissimilarity index)
k. Indicator of racialized socioeconomic segregation (e.g., index of concentrated extremes)

In some embodiments, the graphical intervention test development system 100 may generate one or more variables using artificial intelligence (AI). Such variables may also be referred to as "AI-derived variables". The graphical intervention test development system 100 may use one or more machine learning models (e.g., neural network(s)) to generate an AI-derived variable using data accessed by the graphical intervention test development system 100. For example, the system may generate a set of features using data associated with a test point, and provide the set of features as input to a trained machine learning model (e.g., a trained neural network) to obtain a value of an AI-derived variable for the subject. The graphical intervention test development system 100 may generate AI-derived variables for a subject using data such as patient charts including diagnosis, metastatic status, biomarker status, receipt of therapies, and/or other data. The use of AI-derived variables allows the graphical intervention test development system 100 to leverage more data and create insights from a broader population. Moreover, the AI-derived variables may allow the identification of subjects for inclusion in an intervention test from a broader population. In some embodiments, the graphical intervention test development system 100 may define condition(s) on an AI-derived variable for inclusion of test points in an intervention test and/or generate visualization(s) of an AI-derived variable. The graphical intervention test development system 100 may use the AI-derived variable to identify and characterize cohorts of interest and/or predict likelihood of subjects to be eligible for an intervention test.

In some embodiments, the graphical intervention test development system 110 may be configured to transmit requests for data to an external system. For example, the graphical intervention test development system 110 may transmit queries that, when executed, return requested clinical record data. In another example, the graphical intervention test development system 110 may transmit requests through an application program interface (API). In some embodiments, the graphical intervention test development system 110 may be configured to transmit requests for clinical record data through a communication network (e.g., the Internet).

In some embodiments, the graphical intervention test development system 110 may be configured to store accessed test point data in datastore 118. In some embodiments, the test point data may include clinical record data associated with test points. In some embodiments, the graphical intervention test development system 110 may be configured to organize the storage of the clinical record data by test point. The graphical intervention test development system 110 may be configured to store clinical record data mapped to identifications of test points that the clinical record data is associated with. For example, the graphical intervention test development system 110 may map clinical record data associated with a test point to an identification (e.g., name, test point ID, or other suitable identification) of the test point.

Datastore 118 may comprise any suitable storage hardware. For example, the data storage 118 may comprise of one or more hard drives. In another example, the data storage 118 may comprise cloud storage that may be accessed through a communication network (e.g., the Internet). Clinical record data may be stored in the datastore 118. In some embodiments, the clinical record data may be organized by test point. For example, the clinical record data may be stored in tables. In another example, the clinical record data may be stored without a schema. In some embodiments, datastore 118 or another datastore (not shown) may store information regarding one or more trial sites selected for conducting one or more intervention tests and the test points enrolled or participating in the intervention test(s) at each site.

In some embodiments, datastore 118 may include a database (for example, Flatiron® Health database) that stores clinical record data in the form of longitudinal, de-identified datasets that contain structured, extracted, and derived data elements (for example, real-world endpoints, such as real-world overall survival (rwOS), real-world progression-free survival (rwPFS), real-world time-to-treatment discontinuation (rwTTD) and/or other elements derived from the data) by cancer type. Clinical record data may be de-identified of sensitive information. For example, clinical record data may be de-identified of Protected Health Information in accordance with the Health Insurance Portability and Accountability Act (HIPAA) privacy rule. Real-world overall survival (rwOS) may be defined as time from an index date (e.g., initial diagnosis, advanced diagnosis or the start of a line of therapy) to date of death. Real-world progression-free survival (rwPFS) may be defined as the time from index date (e.g., start date for the desired line of therapy) to either the date of progression or death. Real-world time-to-treatment discontinuation (rwTTD) may be defined as the time from the index date to discontinuation for any reason.

In some embodiments, the datastore 118 may include data accessed from an EHR. In some embodiments, the datastore 118 may include a disease specific database. For example, the database may include data about test points with diagnosis of a particular disease. In some embodiments, the datastore 118 may include multiple such databases each associated with a respective disease. A database may be selected (e.g., for performance of control processing and generation of visualizations) based on a disease for which test points are to be included in an intervention test.

In some embodiments, while datastore 118 is shown as part of the graphical intervention test development system 110 in FIG. 1A, it will be appreciated that datastore 118 may be communicably coupled to the graphical intervention test development system 110 via a communication network. In some embodiments, graphical intervention test development system 110 may be include or be communicably coupled to additional datastore(s) or database(s) that stores one or more rules that may be applied or one or more data models that may be used by the intervention data module 112 to process the clinical record data and/or the intervention test control module 116 to perform the processing and/or analyses described herein.

In some embodiments, intervention data module 112 may be configured to process test point data (e.g., clinical record data) (including information associated with multiple test points) to determine one or more characteristics associated with one or more test points. For example, for a test point diagnosed with Diffuse large B-cell lymphoma (DLBCL), the characteristics may include disease type, demographics and clinical characteristics (e.g., gender, race/ethnicity, age at initial diagnosis, etc.), practice type (community versus academic), year of initial diagnosis, therapy class or number of lines of therapy, group stage at initial diagnosis, cell of origin at initial diagnosis, disease subtype, histology, biomarker statuses, past treatment statuses, ECOG (Eastern Cooperative Oncology Group) Performance Status, and/or other characteristics.

In some embodiments, processing the test point data may include classifying combinations of drugs into therapy classes by applying one or more rules on the test point data. Therapy classes(s) for one or more test points may be determined based on the processing/classification. For example, the intervention data module 112 may classify different combinations of drugs prescribed to a test point into different classes representing the combinations.

In some embodiments, processing the test point data may include determining past treatment statuses by analyzing clinical record data. Past treatment status(es) for one or more test points may be determined based on the analysis. For example, past treatment status(es) may include varying definitions of CAR-T status per line of therapy, varying definitions of Stem Cell Transplant status per line of therapy, varying definitions of radiotherapy status as part of initial treatment, and/or other statuses.

In some embodiments, processing the test point data may include identifying various values of variables indicative of test point health. For example, the intervention data module 112 may identify variable values by analyzing lab results and calculations performed on lab results and/or identifying various valuations of test point health (e.g., ECOG status, biomarker status) found in the clinical record data. In some embodiments, the intervention data module 112 may infer a variable value using a machine learning model. For example, the intervention data module 112 may infer a smoking status of a test point using other data about the test point from the clinical record data to generate input to a machine learning model. The intervention data module 112 may provide the input to the machine learning model to obtain an output indicating the test point's inferred smoking status.

In some embodiments, intervention data module 112 may extract or otherwise determine clinical variable values for test points from test point data (e.g., clinical record data). Example techniques of using machine learning to automatically extract clinical variable values for test points from clinical record data are described in U.S. Patent Application Publication No. US 2021/0027894 entitled "DEEP LEARNING ARCHITECTURE FOR ANALYZING UNSTRUCTURED DATA", which is hereby incorporated by reference in its entirety. Some examples of clinical variables include type of cancer, stage of cancer diagnosis, whether there is metastatic diagnosis, date of metastatic diagnosis, prognosis, and identification of prescribed drugs. In some embodiments, intervention data module 112 may determine one or more test point characteristics using the extracted clinical variable values.

The graphical processing module 114 may be configured to generate various GUIs described herein that provide visualizations of various aspects of intervention test design and assist users 105 in assessing these aspects of intervention test design. For example, the visualizations may allow a user to determine the feasibility of a particular intervention test design. The GUIs may further provide a control interface through which a user may modify control parameters that affect the intervention test design, and view effects of parameter modifications as dynamic updates to visualizations rendered in response to parameter modifications. The updates may inform how modifications affect the intervention test. Graphical processing module 114 may be configured to generate the GUIs based on the information processed by the intervention data module 112 and/or processing or control processing performed by the intervention test control module 116.

As shown in FIG. 1A, graphical processing module 114 may be configured to generate graphical intervention test development environment GUI 120. GUI 120 may include at least a first GUI portion 122 and a second GUI portion 124. The first GUI portion 122 may include a first GUI element 132 configured to receive input indicating selection of a set of test points. A set of test points may also be referred to herein as a "cohort". In some embodiments, first GUI element 132 may include a drop-down menu including a list of selectable options for different test point sets, such as point set 1, point set 2, and/or other options. The first GUI portion 122 may include a second GUI element 134 configured to receive input indicating control processing to be performed on clinical record data associated with a group of test points in the test point set selected via the first GUI element 132. In some embodiments, second GUI element 134 may include a drop-down menu including a list of selectable options for different types of control processing. A type of control processing may also be referred to as "analysis type". In FIG. 1A, the control processing types include, processing 1, processing 2, processing 3, and/or other options. Examples of control processing may include, but not be limited to, cohort optimization, identifying patterns of care, determining real-world overall survival, determining enrollment projections, and/or other processing.

In some embodiments, in response to receiving user input via the first GUI element 132 indicating a selection of a particular set of test points and via the second GUI element 134 indicating a selection of a control processing to be performed for the selected set of test points, the graphical processing module 114 may generate one or more visualizations including information about the selected set of test points and the selected control processing. Example of such visualizations are described herein with reference to FIG. 11-FIG. 19, and FIG. 23-FIG. 25

Figure 1B:
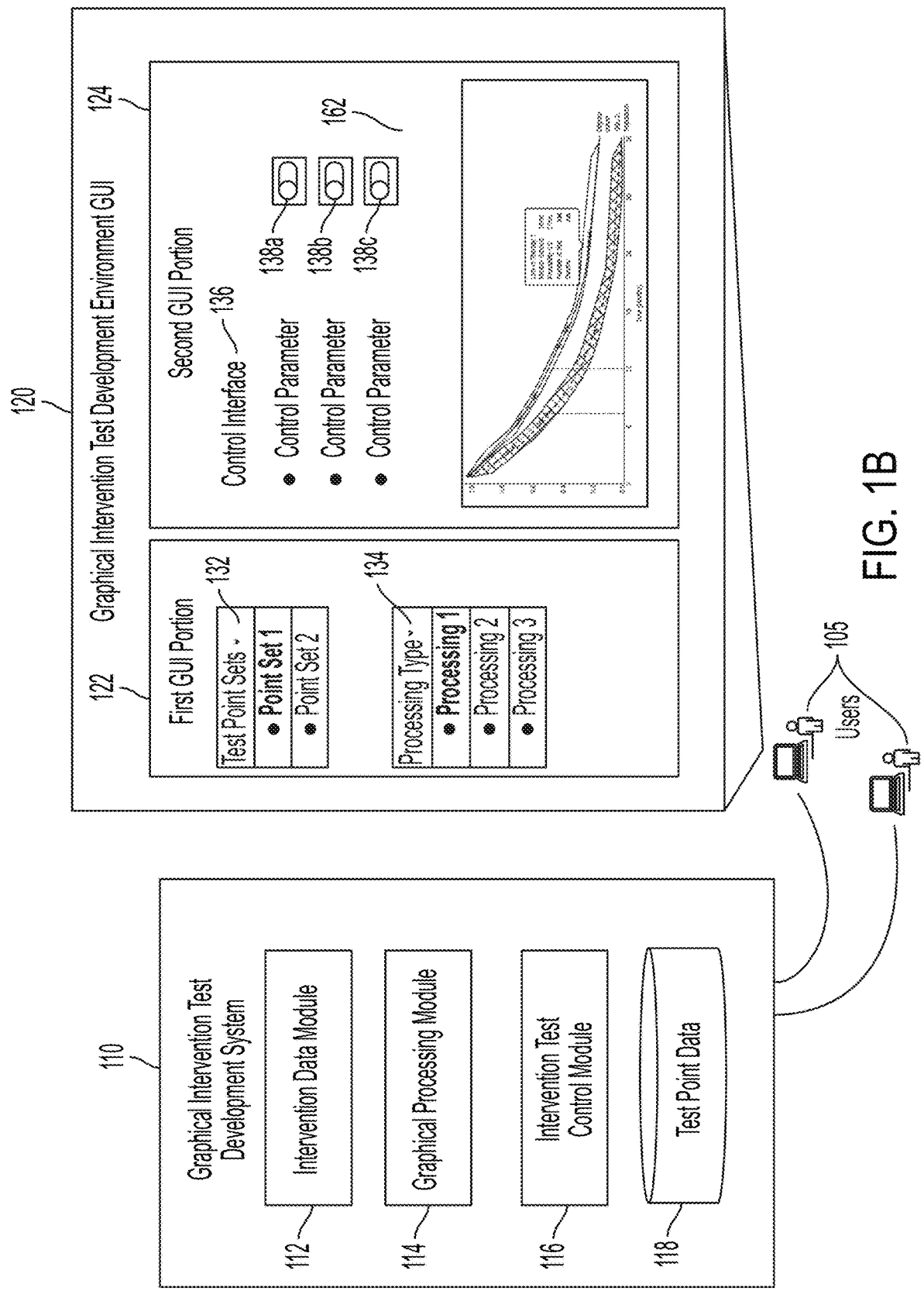
FIG. 1B-1D are illustrative diagrams of a graphical intervention test development environment that may be generated by the graphical intervention test development system of FIG. 1A, according to some embodiments of the technology described herein.

For example, user input indicating a selection of "point set 1" and "processing 1" in the first GUI portion 122 of GUI 120 may cause the graphical processing module 114 to generate a visualization 162 in second GUI portion 124 as shown in FIG. 1B. In some embodiments, "processing 1" may correspond to a "cohort optimization" processing that assesses an impact of one or more control parameters on the overall intervention test design. In some embodiments, cohort optimization may include assessing an impact of condition(s) for inclusion of test points and enrollment statistics. In some embodiments, cohort optimization control processing may include suggesting or recommending changes to condition(s) in a way that increases the eligible test point population for the intervention test without negatively impacting measures of performance such as hazard ratio. In some embodiments, the GUI portion 124 may be configured to display multiple different types of visualizations. Examples of a visualization 162 that may be generated from executing processing 1 are described herein with reference to FIGS. 11-18.

In some embodiments, the GUI portion 124 may include a control interface 136 that allows a user to modify control parameters for the intervention test. In the example of FIG. 1B, the control interface 136 allows a user to modify control parameters that control a set of conditions (also referred to as "eligibility criteria") for inclusion of test points in the intervention test. In some embodiments, for each condition in the set of conditions, the control interface 136 may include information indicating a number of test points in point set 1 that satisfy the condition. One or more of the control parameters may be manipulated via GUI elements 138a, 138b, 138c. A user may manipulate GUI element 138a, such as a toggle switch by toggling it to the right. This manipulation triggers a change to a first condition that indicates a change to the number of test points in point set 1 that satisfy the first condition. For example, in response to an update in the first condition using element 138a, the intervention data module 112 may recompute a number of test points in point set 1 using the updated first condition and the recomputed number of test points may be displayed in the GUI 120 (e.g., by the graphical processing module 114).

Figure 1C:
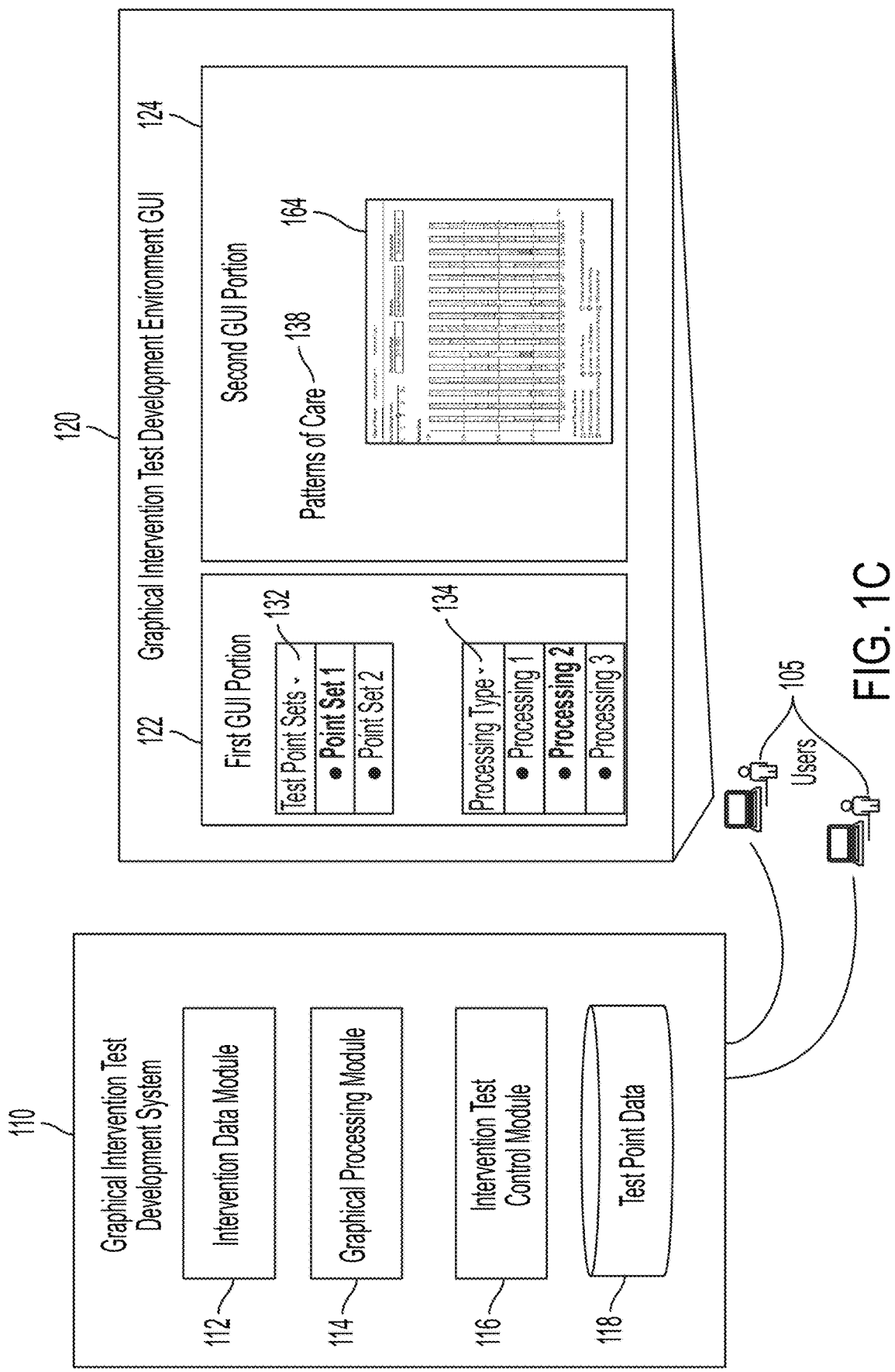

As another example, user input indicating a selection of "point set 1" and "processing 2" in the first GUI portion 122 of GUI 120 may cause the graphical processing module 114 to generate a visualization 164 in second GUI portion 124 as shown in FIG. 1C. In some embodiments, "processing 2" may correspond to a "patterns of care" control processing that assesses patterns of care associated with point set 1. In some embodiments, the control processing may include assessing contemporaneous patterns of care for test points with a particular disease (e.g., DLBCL) in point set 1. Visualization 164 may include information regarding patterns of care for the group of test points in point set 1. For example, the visualization 164 may graphically illustrate a distribution of therapy classes of types for treatment of the particular disease. An example of a visualization generated as a result of executing patterns of care control processing is described herein with reference to FIG. 18.

Figure 1D:
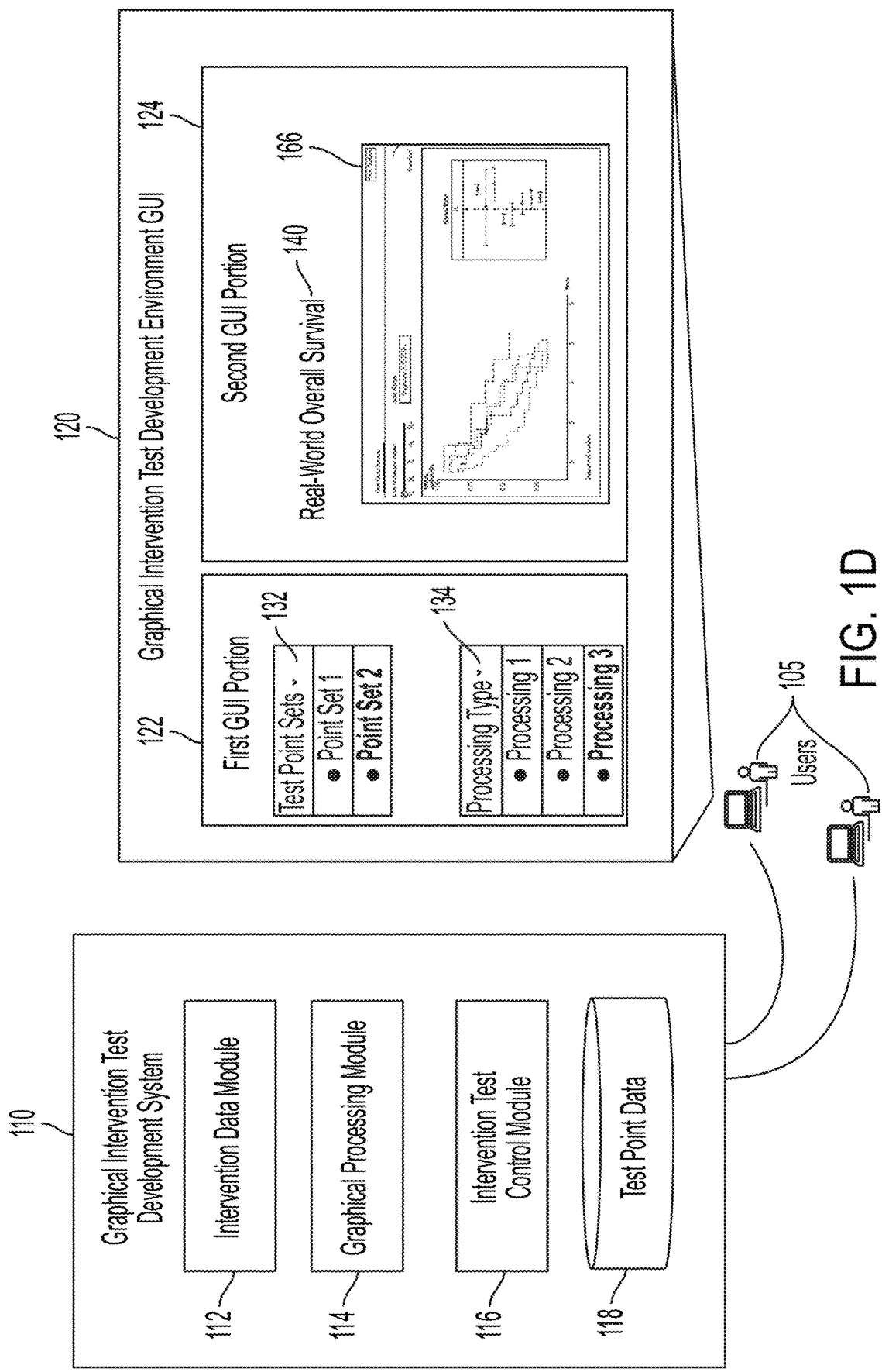

As yet another example, user input indicating a selection of "point set 2" and "processing 3" in the first GUI portion 122 of GUI 120 may cause the graphical processing module 114 to generate a visualization 166 in second GUI portion 124 as shown in FIG. 1D. In some embodiments, "processing 3" may correspond to a "real-world overall survival" control processing that assesses the real-world overall survival associated with point set 2. In some embodiments, real-world overall survival control processing may include assessing real-world overall survival (rwOS) for different patterns of care in test points in point set 2 with a particular disease, such as DLBCL to, for example, inform endpoints for the intervention test and calculate sample size and statistical power. Visualization 166 may include information regarding real-world overall survival for the group of test points in point set 2. An example of the visualization 166 is described herein with reference to FIG. 19.

In some embodiments, intervention test control module 116 may perform the various types of control processing, such as cohort optimization, patterns of care, real-world overall survival, enrollment projections, and/or other control processing described herein. Intervention test control module 116 may process test point data based on selection of a set of test points and control processing via GUIs described herein. For example, selection of a set of test points and control processing may trigger the intervention test control module 116 to perform the selected control processing on clinical record data associated with test points in the selected set.

Figure 2:
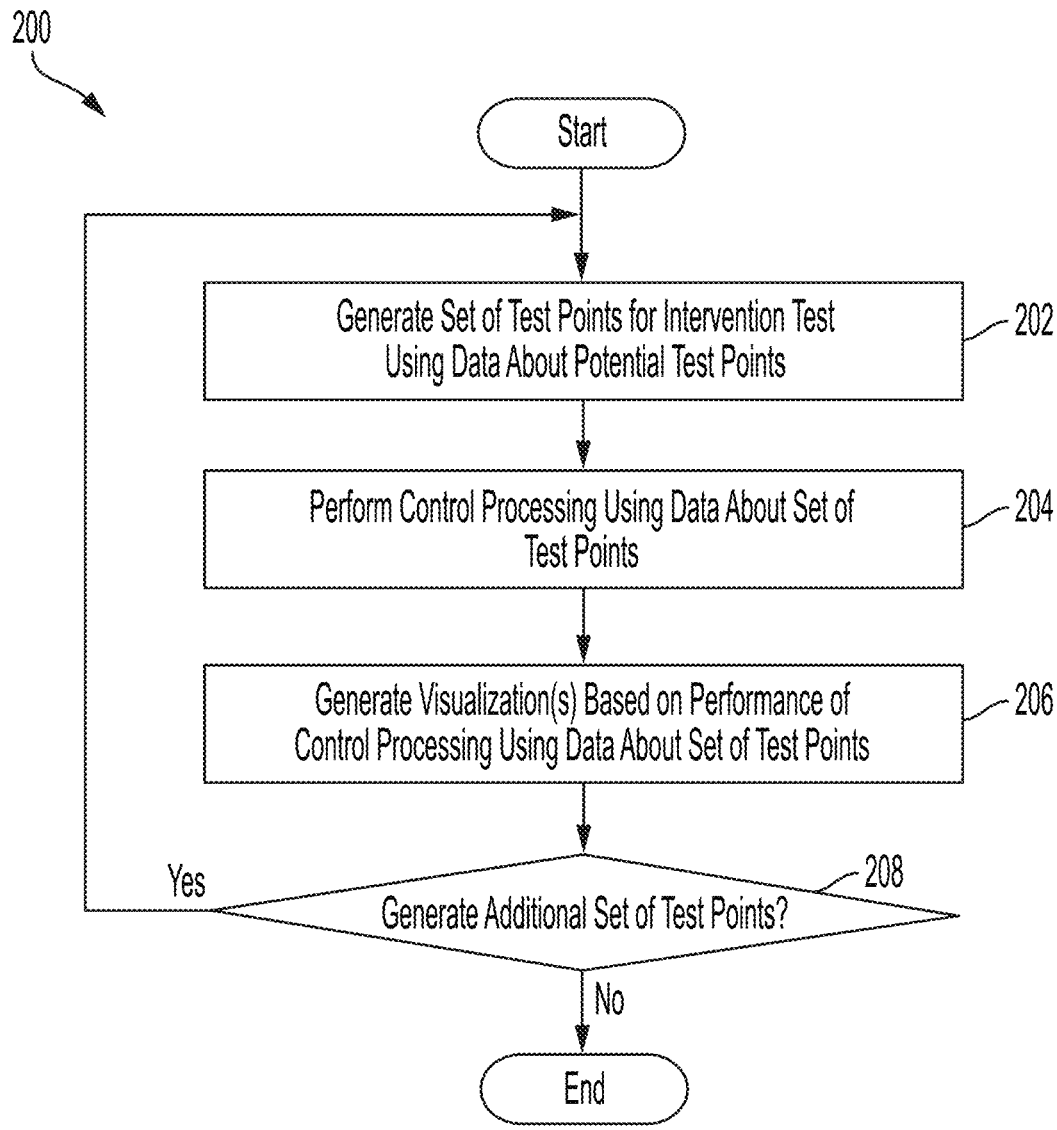
FIG. 2 is a flowchart of an example process of generating one or more visualizations of an intervention test in a graphical intervention test development environment, according to some embodiments of the technology described herein.

FIG. 2 is a flowchart of an example process 200 of generating one or more visualizations of an intervention test in a graphical intervention test development environment, according to some embodiments of the technology described herein. The visualization(s) facilitate a user's development of the intervention test (e.g., by allowing the user to assess aspects of the intervention test's design and modifications to the design). Thus, the graphical intervention test development environment allows a user to graphically design the intervention test. Process 200 may be performed by any suitable computing device. For example, process 200 may be performed by the graphical intervention test development system 110 described herein with reference to FIGS. 1A-1D.

In some embodiments, the system may access an intervention test. The system may access an intervention test by generating a new intervention test or accessing a previously generated intervention test stored by the system. In some embodiments, the system may provide a GUI in the environment through which the user may provide input commanding generation of a new intervention test or accessing a previously generated intervention test. FIG. 4 is an illustrative GUI 400 through which a user can access an intervention test, according to some embodiments of the technology described herein. As shown in FIG. 4, the example GUI 400 includes a "Create New Study" button in GUI 400 to initiate generation of an intervention test. The GUI 400 also includes a list of graphical elements representing previously generated intervention tests (e.g., "Study name 1", "Study name 2", "Study name 3", etc.).

Figure 5:
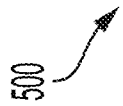
FIG. 5 is an illustrative GUI generated for generation of a new intervention test in a graphical intervention test development system, according to some embodiments of the technology described herein.

In some embodiments, the system may initiate generation of a new intervention test (e.g., in response to selection of the "Create New Study" button in GUI 400). The system may determine a name of the new intervention test. In some embodiments, the system may provide a GUI through which the user may provide input indicating a name of the new intervention test. FIG. 5 is an illustrative GUI 500 for generation of a new intervention test, according to some embodiments of the technology described herein. GUI 500 includes a window 502 that allows a user to input a name for the new intervention test. In the example of FIG. 5, the user has entered a new intervention test name of "Study X-1". Selection of the "Create Study" button in window 502 may cause the system to generate a data record identified in the system by the name specified in the window 502. For example, the system may generate a profile for the new intervention test that stores information (e.g., control parameter values) specifying a design of the intervention test.

Process 200 begins at act 202, where the system generates a set of test points (e.g., a cohort) for an intervention test or study test point using stored data about potential test points (e.g., stored in datastore 118 described herein with reference to FIGS. 1A-1D). In some embodiments, generating a set of test points comprises determining which of the potential test points satisfy a set of conditions (e.g., eligibility criteria) for inclusion in the intervention test, and determining test points that meet the set of conditions to be the set of test points. For example, the set of conditions may include one or more conditions on clinical data associated with the test points. As another example, the set of conditions may include one or more conditions on socioeconomic variables associated with the test points. In some embodiments, the system may access a set of control parameters associated with the intervention test that indicate a set of conditions for inclusion in the intervention test. The system may determine, using the data about the potential test points, a set of test points that meet the set of conditions indicated by the control parameters. The system may generate a data record (e.g., table, file, document, or other type of data storage structure) that stores data about the set of test points (e.g., for subsequent use in generating visualizations of aspects of the intervention test).

Figure 6:
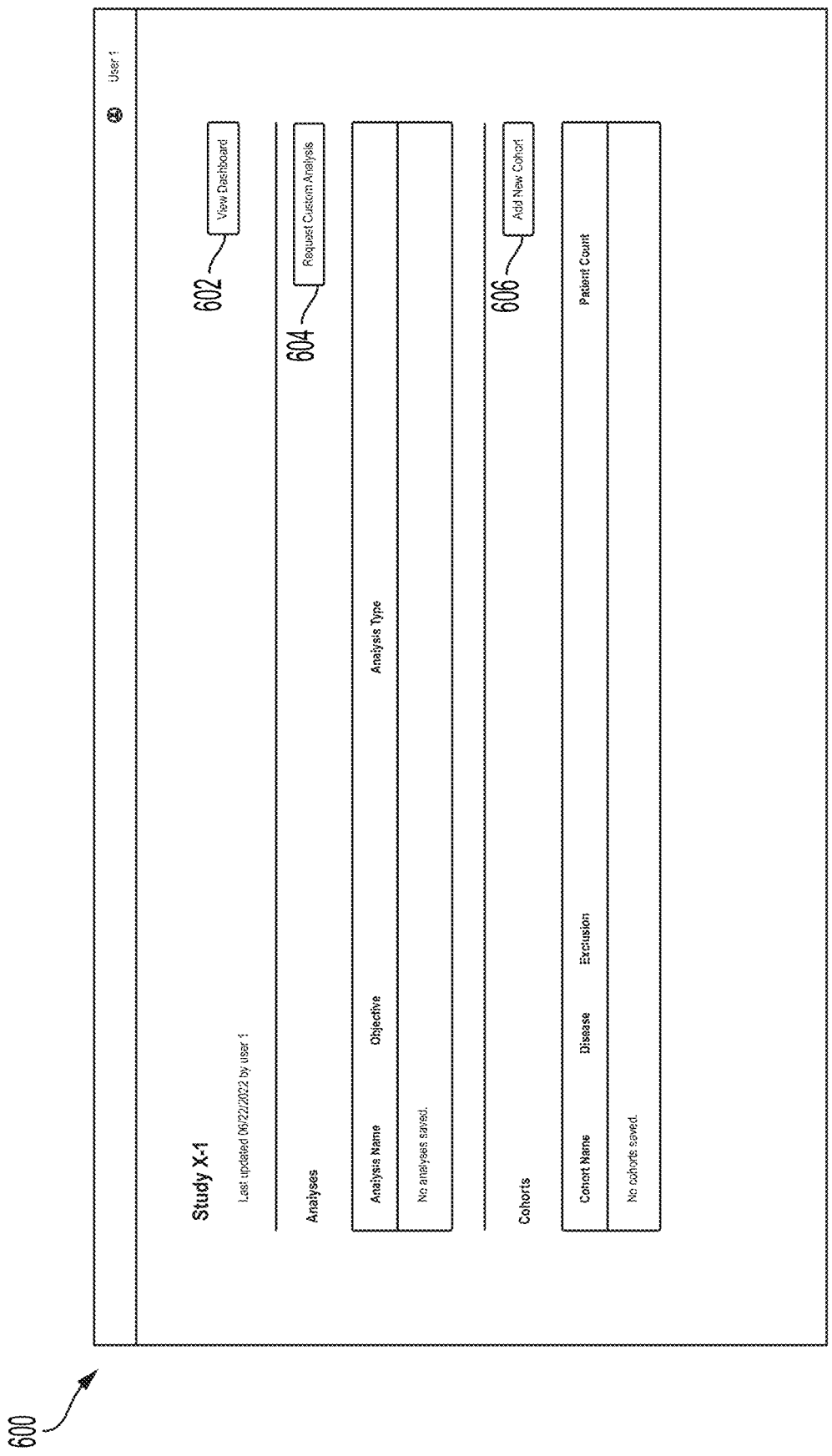
FIG. 6 is an illustrative GUI through which a user may view an intervention test profile, according to some embodiments of the technology described herein.

In some embodiments, the system may provide a GUI in the graphical intervention test development environment through which a user may initiate generation of a set of test points. FIG. 6 shows an example GUI 600 that may be generated by the system. In the example of FIG. 6, a user may initiate a process of generation of a set of test points for an intervention test by selecting GUI element 606 (i.e., "Add New Cohort" button) in GUI 600. Selection of the GUI element 606 may provide a GUI in the graphical intervention test development environment through which the system may receive user input specifying control parameters that indicate the set of conditions for the intervention test.

GUI 600 shown in FIG. 6 illustrates a profile view of an intervention test (e.g., an intervention test accessed through GUI 400 described herein with reference to FIG. 4). The profile view includes information regarding one or more sets of test points generated for the intervention test and one or more control processes (e.g., "Analyses") to be performed on clinical record data associated with test points in the set(s) of test points. GUI 600 may include GUI element 602

("View Dashboard" button), GUI element 604 ("Request Custom Control processing" button), and GUI element 606 ("Add New Cohort" button). Selection of GUI element 606 may cause the system to generate a GUI through which a user may provide input indicating control parameters to generate a set of test points for inclusion in the intervention test.

FIG. 7 is an illustrative GUI 700 through which a user may specify control parameters to generate a set of test points (e.g., a cohort) for an intervention test, according to some embodiments of the technology described herein. A cohort may have a name identifying the cohort, a disease or EHR database from which to access data (e.g., clinical record data) about potential test points, and conditions for inclusion of test points in the intervention test (e.g., inclusion/exclusion criteria). In some embodiments, an intervention test may include cohorts for various different diseases. GUI 700 includes various fields through which a user may specify control parameters indicating a set of conditions for inclusion of test points in the intervention test. GUI 700 includes a field 710 (e.g., a text field) through which the system may receive a name to be assigned to a set of test points generated based on the set of conditions. GUI 700 includes a dropdown list 712 for receiving a selection of a particular disease (e.g., DBCL) that is shared by test points in the set.

GUI 700 includes various GUI elements that allow the specification of control parameter values indicating condition(s) for participation in the intervention test. For example, one or more control parameters may specify a filter that includes or excludes test points in a cohort for an intervention test. Example filters may include, but not be limited to, test points included in a particular database, test points having a line of therapy initiated in a certain time period, or test points having a line of therapy initiated after a certain date in time, test points having received radiotherapy as part of initial treatment, and/or other filters.

As shown in FIG. 7, GUI 702 may include GUI elements to set control parameters indicating condition(s) for inclusion in an intervention test. A condition may be used to include test points or exclude test points. The GUI 700 includes GUI elements 724, 726, 728, 730, and 732 through which a user provides input indicating the following condition: the initial diagnosis date of the test point is in a time period between a date specified by element 730 and a date specified by element 732. The selection of the radio button 720a that test points meeting this condition are to be included in the intervention test. Alternatively, the selection of radio button 722a would exclude test points meeting the condition from the intervention test. As another example, GUI 700 includes an element 734 that allows the user to specify a condition based on therapy class, and the element 736 to specify a particular therapy class. The user input shown in FIG. 7 indicates the following condition: test point is being treated under the maintenance therapy class. Selection of the radio button 722b specifies that test points meeting the condition specified by GUI elements 734, 736 are to be excluded from the intervention test. Alternatively, selection of the radio button 720b would specify that test points meeting the condition specified by GUI elements 734, 736 are to be included in the intervention test. Selection of GUI element 738 (the "Save Cohort" button) may trigger generation of a set of test points for the intervention test.

In some embodiments, the system may generate a set of test points for an intervention test based on characteristic(s) of test points(s) determined from data about potential test points (e.g., by intervention data module 112 using clinical record data associated with the test points). The system may use the data to determine which test points meet a set of conditions (e.g., specified through GUI 700 described herein with reference to FIG. 7). For example, the system may determine characteristics of a test point diagnosed with DLBCL, such as disease type, demographics and clinical characteristics (e.g., gender, race/ethnicity, age at initial diagnosis, etc.), year of initial diagnosis, therapy class or number of lines of therapy, socioeconomic variable(s) and/or other characteristics. The system may use the determined characteristics to determine which test points meet the set of conditions. For example, based on the set of conditions specified in GUI 700, the system may generate a set of test points that: (1) includes test points with an initial diagnosis of DLBCL in a date range specified in the GUI 700; and (2) excludes test points that are being treated under the maintenance therapy class.

Figure 8:
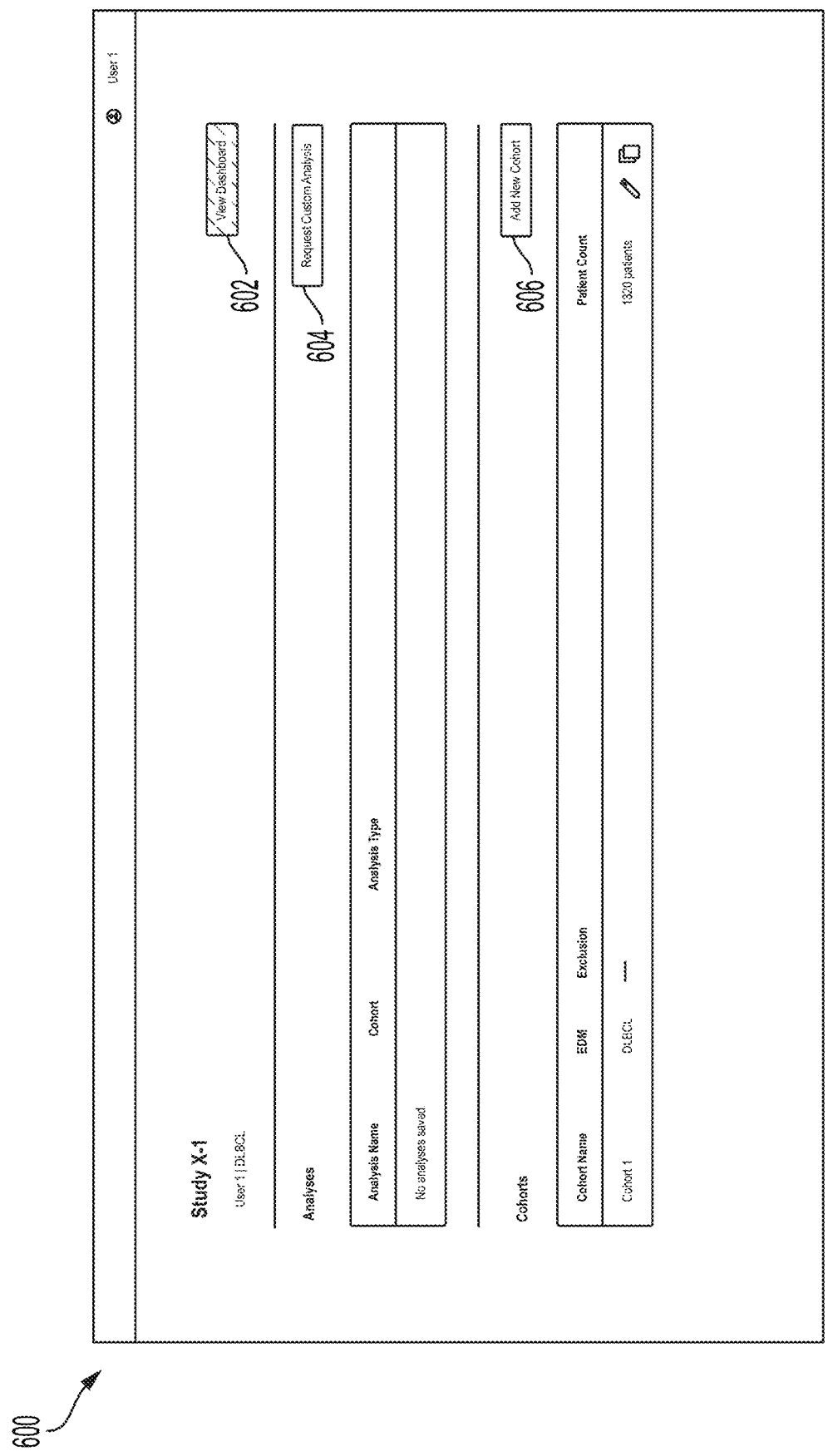
FIG. 8 is an illustrative GUI showing an update to an intervention test to include a newly created set of test points, according to some embodiments of the technology described herein.

Once the set of test points is generated for the intervention test, the system may add the set of test points to a data record storing information about the intervention test (e.g., to a profile storing information about the intervention test). FIG. 8 shows the GUI 600 updated after addition of the set of test points "Cohort 1" to the intervention test "Study X-1". For example, the set of test points "Cohort 1" may have been created using the set of conditions specified through GUI 700 described herein with reference to FIG. 7. As shown in FIG. 8, the "Cohorts" section of the GUI 700 now lists "Cohort 1" as a set of test points included in the intervention test. Additional sets of test points may be created for the intervention test by selecting GUI element 606 and defining cohort parameters and/or eligibility criteria for the additional studies via GUI 700 as described above.

Figure 10:
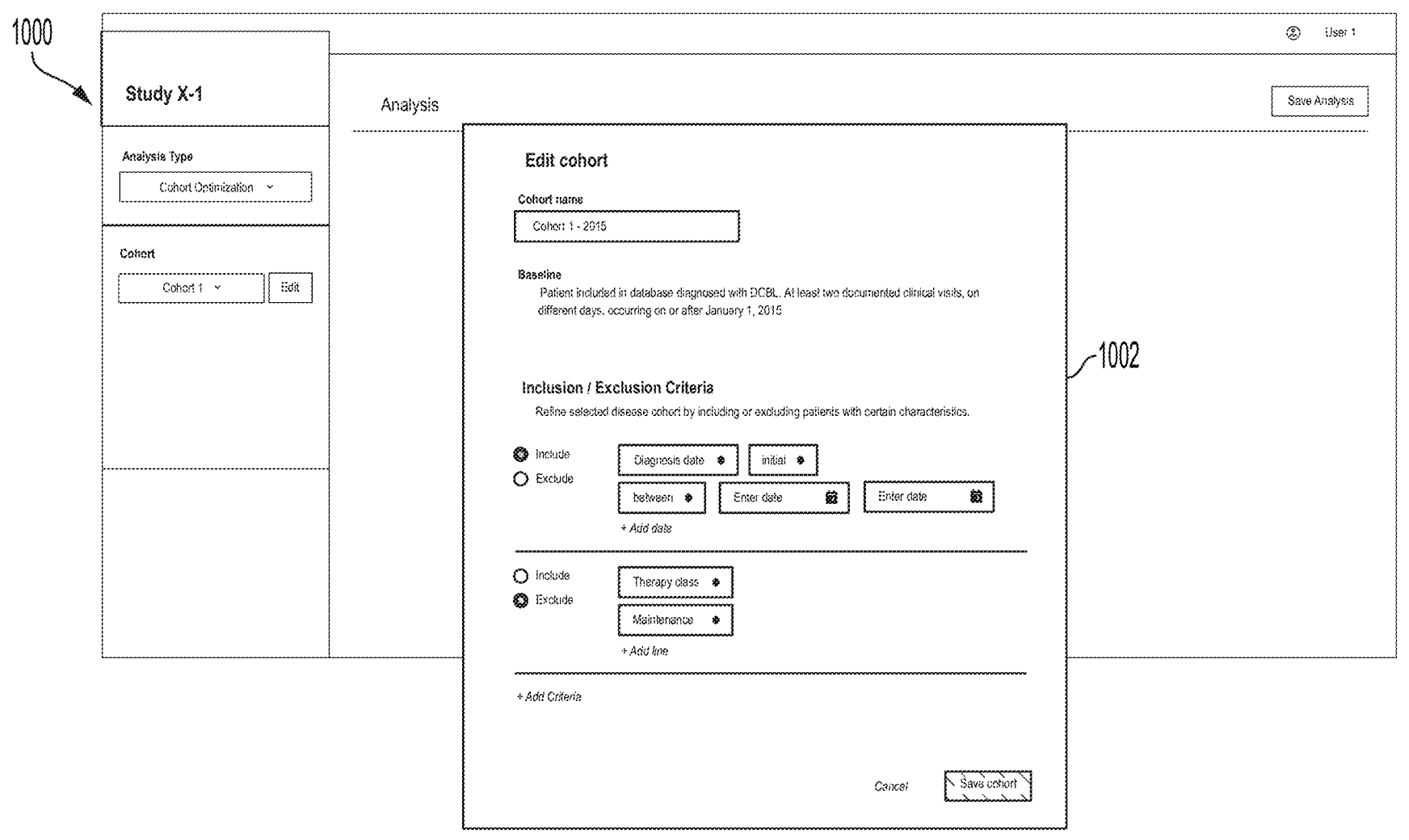

In some embodiments, the system may modify a previously generated set of test points. The system may provide a GUI through which a user may edit the previously generated set of test points. The GUI may allow modification of control parameter(s) that indicate condition(s) for inclusion of test points in the intervention test. FIG. 10 is an illustrative GUI 1000 through which a user may modify one or more control parameters to change a set of test points, according to some embodiments of the technology described herein. As shown in FIG. 10, the edit cohort GUI 1002 is similar to the add new cohort GUI 702 and includes various GUI elements that are configured to receive input indicating changes to parameters of the cohort and/or eligibility criteria for participation in the intervention test. In some embodiments, the edit cohort GUI 1002 may be generated in response to receiving input indicating selection of the "Edit" button next to the cohort selection GUI element 904 in the GUI 900 shown in FIG. 9.

Next, process 200 proceeds to act 204, where the system performs control processing on a set of test points included in the intervention test. The system may perform control processing using data (e.g., clinical record data) about the set of test points to determine characteristics of the intervention test based on control parameters (e.g., that indicate condition(s) for inclusion of test points) configured for the intervention test. For example, the system may use data about the set of test points accessed from a database storing data extracted from an HER and/or data derived therefrom. As another example, the system may use data about the set of test points accessed from a database associated with a particular disease (e.g., that the set of test points have been diagnosed with) and/or data derived therefrom. The system may use the determined characteristics of the intervention test to generate visualizations of different aspects of the intervention test.

In some embodiments, the system may perform different types of control processing to determine different characteristics of the intervention test. For example, the system may perform control processing to determine an overall survival of the set of test points. As another example, the system may perform control processing to determine real-world overall survival of the set of test points. As another example, the system may perform control processing to determine a distribution of test points across one or more intervention test sites. As another example, the system may perform control processing to determine a pattern of intervention associated with the set of test points.

In some embodiments, the system may determine various different characteristics of the intervention test from performance of control processing. Examples of characteristics that may be determined from performance of control processing include a total number of the set of test points included in the intervention set, a number of the set of test points that meet each of a set of conditions for inclusion in the intervention test, a survival curve for the set of test points, number of test points at different intervention test sites, a number of the set of test points that have been diagnosed with each of a set of diseases, demographic information about the set of test points (e.g., age distribution, gender distribution, race distribution, ethnicity distribution, geographic region distribution, practice type distribution, and/or other demographic information), a diversity metric (e.g., diversity score), distribution of therapy class, real world survival probability and statistics, hazard ratio, counts of various test point categories (e.g., black test point count, Latinx candidate count, low socioeconomic status (SES) test point count, geocoded address, etc.), and/or other characteristics.

Figure 9:
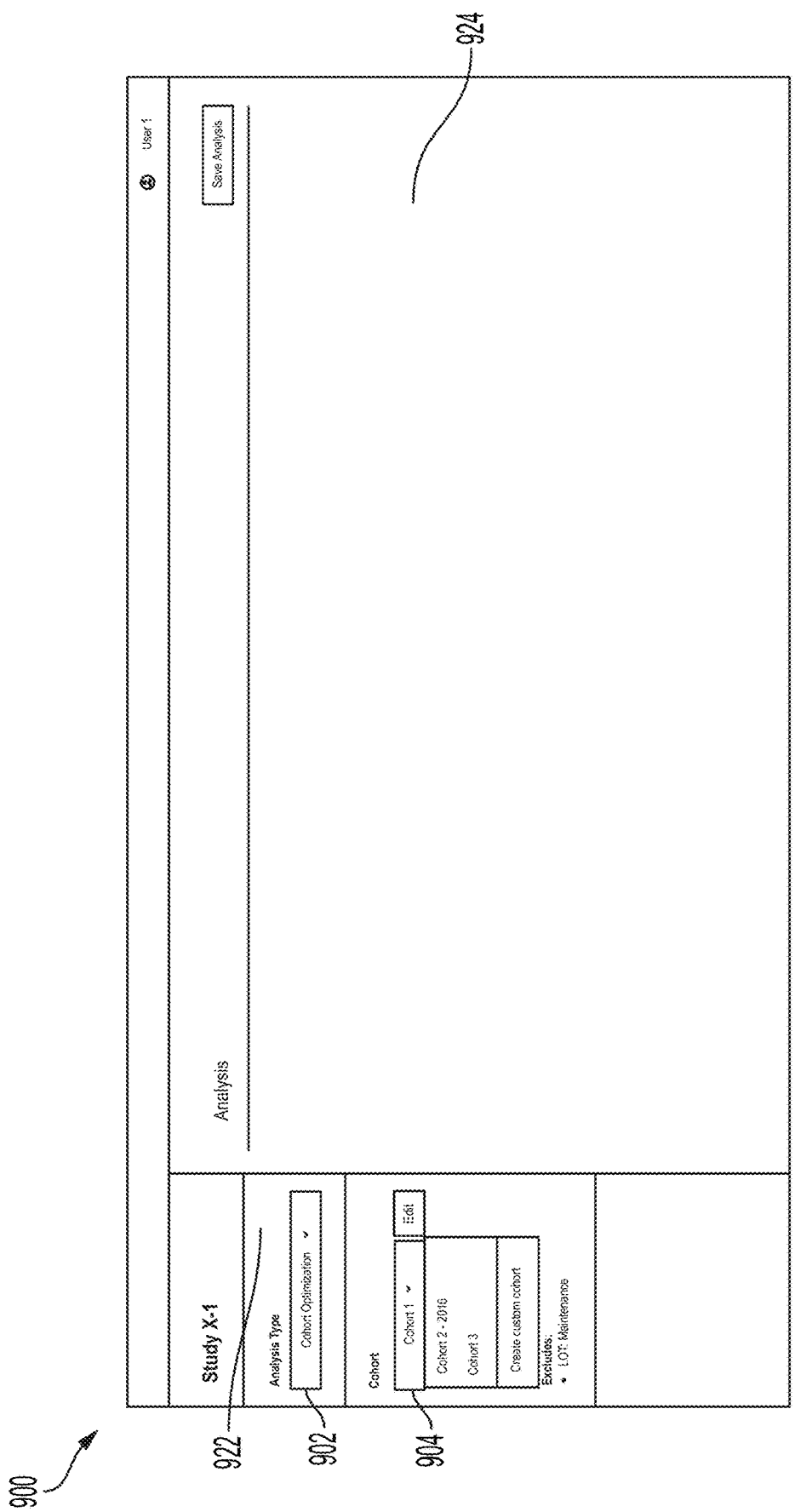
FIG. 9 is an illustrative GUI that allows a user to select a set of test points in an intervention test and control processing to be performed on the selected set of candidates, according to some embodiments of the technology described herein.

In some embodiments, the system may determine control processing to perform and a set of test points of an intervention test on which to perform the control processing. The system may determine the control processing to be performed and set of test points based on user input received through a GUI provided in the graphical intervention test development environment. FIG. 9 is an illustrative GUI 900 that allows a user to select a set of test points in an intervention test and control processing to be performed for the selected set of test points, according to some embodiments of the technology described herein. GUI 900 includes a section 922 including a GUI element 902 (e.g., a dropdown list) through which a user may select a type of control processing (e.g., "Analysis Type") to be performed. Example types of control processing that may be performed by the system are described herein. The section 922 includes a graphical element 904 (e.g., a dropdown list) through which a user may select a set of test points (e.g., a cohort) for which to perform the selected control processing.

Next, process 200 proceeds to act 206, where the system generates one or more visualizations based on the performance of the control processing. The system may generate the visualization(s) by: (1) obtaining characteristics of the intervention test determined from execution of the control processing; and (2) generate the visualization(s) using the obtained characteristics.

In some embodiments, the visualization(s) may be displayed in GUI(s) of the graphical intervention test development environment described herein. The visualization(s) may assist a user in configuring various aspects of the intervention test's design and assessing various aspects of the intervention test's design and feasibility of the design. For example, the visualizations generated by the system may enable the evaluation of anticipated intervention test outputs (e.g., evaluation of protocol design to anticipate intervention test outcomes, such as natural history of disease, treatment outcomes, adaptive design, etc.). As another example, the visualizations generated by the system may enable assessing an impact of changes to the protocol (e.g., assessing the impact of potential design decisions on outcomes, treatment, and/or events, such as changing eligibility criteria, schedule of assessments, etc.) on outcomes, treatment, and/or events. As yet another example, the visualizations generated by the system may enable definition of endpoints and sample sizes (e.g., providing real-world overall survival (rwOS), real-world time to treatment discontinuation (rwTTD), and/or real-world progression free survival (rwPFS) insights to inform selection of protocol endpoints, appropriate statistical power, and resulting intervention test size). As a further example, the visualizations generated by the system may enable selection of potential intervention test sites (e.g., inform selection of potential trial sites by leveraging RWD to estimate the potentially eligible population at research sites, conduct inclusion/exclusion sensitivities, and enrich for diversity).

In some embodiments, the system may include, in a GUI displaying the visualization(s), a control interface through which the system may receive modifications in control parameters. For example, the system may provide a control interface through which a user may provide input indicating changes in one or more control parameters that determine condition(s) for the inclusion of test points in the intervention test. The system may dynamically update the visualization(s) responsive to the manipulation of control parameter(s) through the control interface. In some embodiments, the system may generate, in a GUI displaying the visualization(s), a recommended modification to one or more control parameters. For example, the system may generate a graphical element displaying a message indicating a change to control parameter(s) that would improve representation of a certain segment of the population while.

Returning to FIG. 2, process 200 proceeds to act 208, where the system determines whether an additional set of test points is to be generated for the intervention test. For example, the additional set of test points may be generated in order to design additional study arms or evaluate additional condition(s) for inclusion and their impact on eligibility for the intervention test. As another example, the system may generate an additional set of test points to ensure that another subset of a population is adequately represented in the intervention test. The system may determine whether an additional set of test points is to be generated based on user input (e.g., selection of the "Add New Cohort" button in GUI 600). In response to user input indicating a command to generate an additional set of test points, the system may return to act 202 where the system generates an additional set of test points for the intervention test.

FIGS. 11-19 illustrate various visualizations that may be generated by the system performing process 200, according to some embodiments of the technology described herein.

Figure 11:
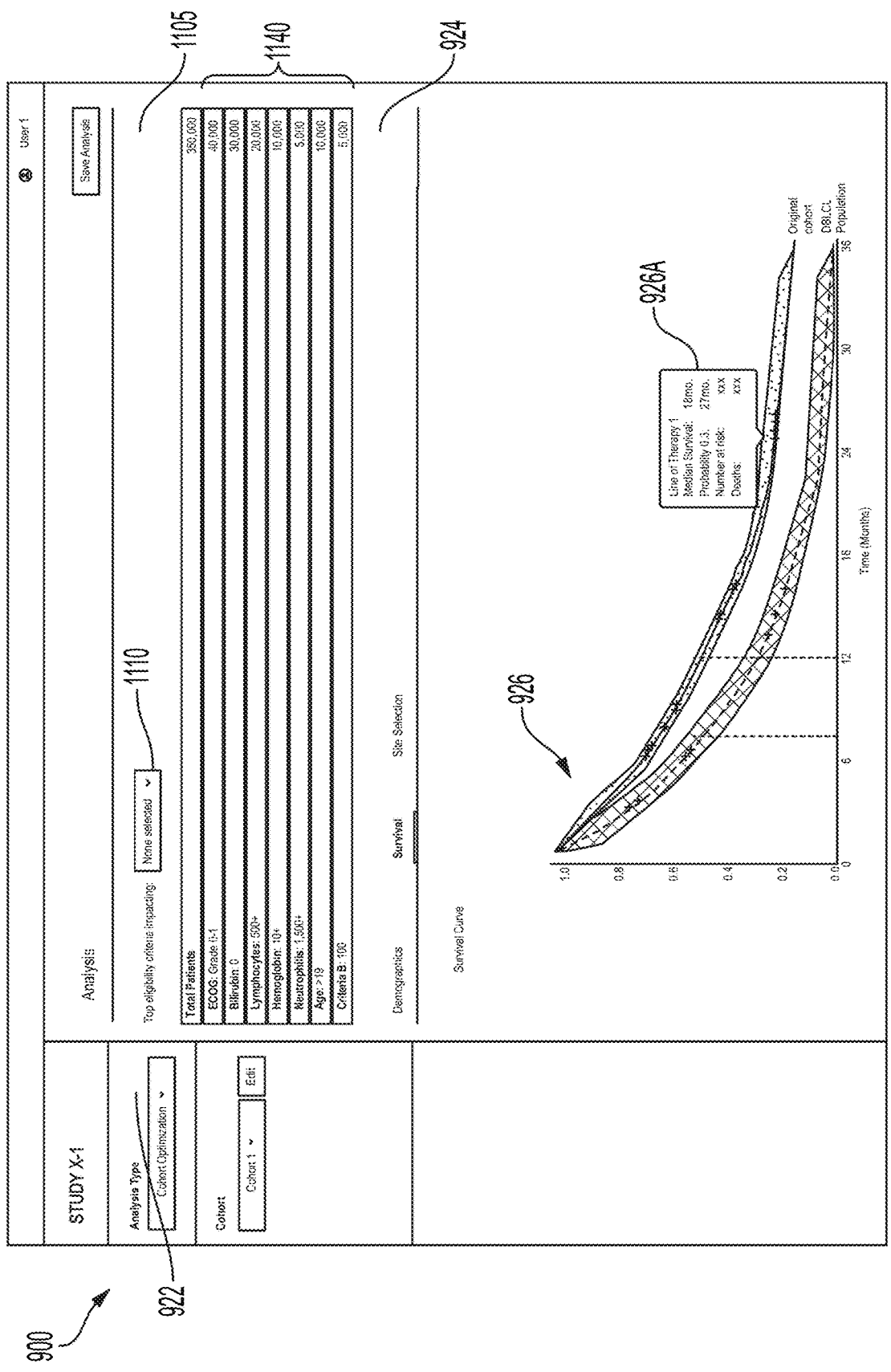
FIG. 11 is an illustrative GUI showing a visualization of survival for a set of test points in an intervention test, according to some embodiments of the technology described herein.

FIG. 11 is the GUI 900 showing a visualization of survival for the set of test points in the intervention test, according to some embodiments of the technology described herein. As shown in FIG. 11, an upper area of the second GUI portion 924 shows a total number of test points (e.g., 350,000) in the set of test points included in the intervention test (e.g., that satisfy a set of conditions for inclusion in the intervention test). The GUI portion 924 includes a listing 1140 of conditions (e.g., ECOG status, bilirubin level, lymphocytes level, hemoglobin level, neutrophils, age, and/or other criteria). The listing 1140 indicates a number of test points in the set of test points that satisfy each condition.

As shown in FIG. 11, the GUI 900 shows a generated visualization of survival rate for the intervention test. The lower area of the second GUI portion 924 shows a survival curve 926 showing the overall survival rate of the set of test points having a disease in relation to the overall survival rate of the population having the disease. The system may have determined survival rate values from performing control processing, and generated the graph 926 using the determined survival rate values (e.g., by extrapolation using the survival rate values). The graph 926 includes a graphical element 926A that indicates median survival of the set of test points, a number of months at which the survival rate is 0.3, a number of the set of test points at risk of death, and a number of deaths in the set of test points. The visualization of FIG. 11 may, for example, be used by a user to determine whether the set of test points adequately represents the general population in terms of survival. As another example, the visualization may be used by a user to determine whether the set of test points meets a target deviation from the general population in terms of survival.

Figure 12:
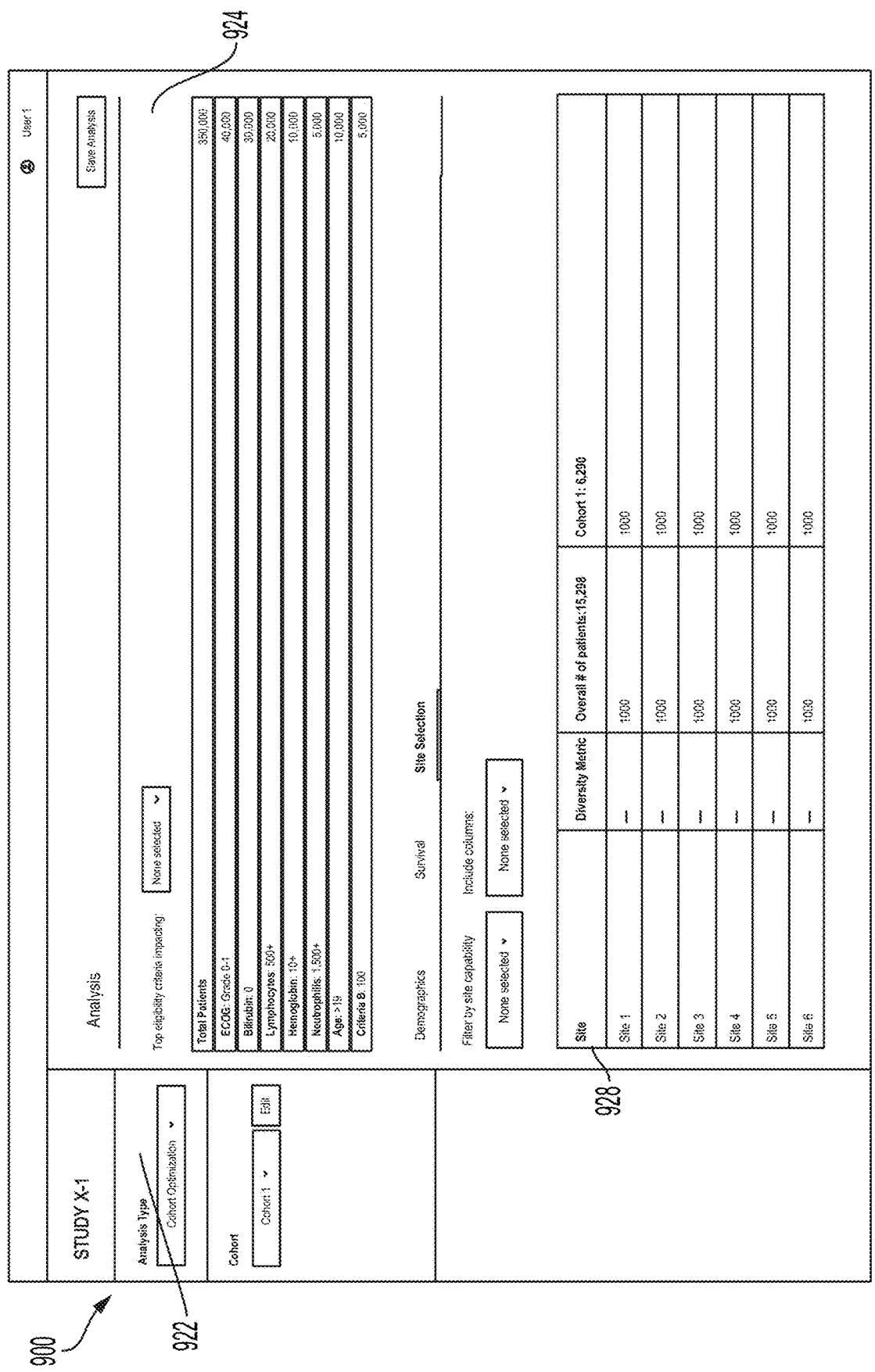
FIG. 12 is an illustrative GUI showing a visualization of intervention test site information, according to some embodiments of the technology described herein.

In some embodiments, an intervention test may include multiple different intervention test sites. When performing one type of control processing, the system may process clinical record data associated with test points in the selected set and/or intervention test site-related data to determine, for each site of the intervention test sites, a number of the set of test points at the intervention test site. The system may generate a visualization that includes the determined site information. FIG. 12 is the GUI 900 showing a visualization of intervention test site information, according to some embodiments of the technology described herein. FIG. 12 includes a table 928 with site-related information including a diversity metric for each site listed in the table. The table 928 includes an entry for each of multiple intervention test sites. For each intervention test site entry, the table includes a site name, a diversity metric (e.g., a score), a number of total test points at the intervention test site, and a number of the set of test points included in the intervention test at the intervention test site. The table 928 provides a user a visualization of a distribution of the set of test points included in the intervention test across the set of intervention test sites relative to a distribution of all test points across the intervention sites. The visualization may, for example, allow a user to determine whether the set of test points accurately reflects the distribution of all test points across the various intervention test sites.

In some embodiments, each intervention site may be sites from which the system has permission to identify certain characteristics for test points at the site. For example, the system may have permission to identify names of test points at the site. As another example, the system may have permission to determine test point counts of test points at the site. The system may access a fraction of test points at a given site. The system may use the fraction to determine how many total test points are at the given site (e.g., by multiplying the number of test points accessible to the system by an inverse of the fraction). The system may perform a similar technique for various subsets of test points (e.g., black, Latinx, and/or other subsets).

Figure 13:
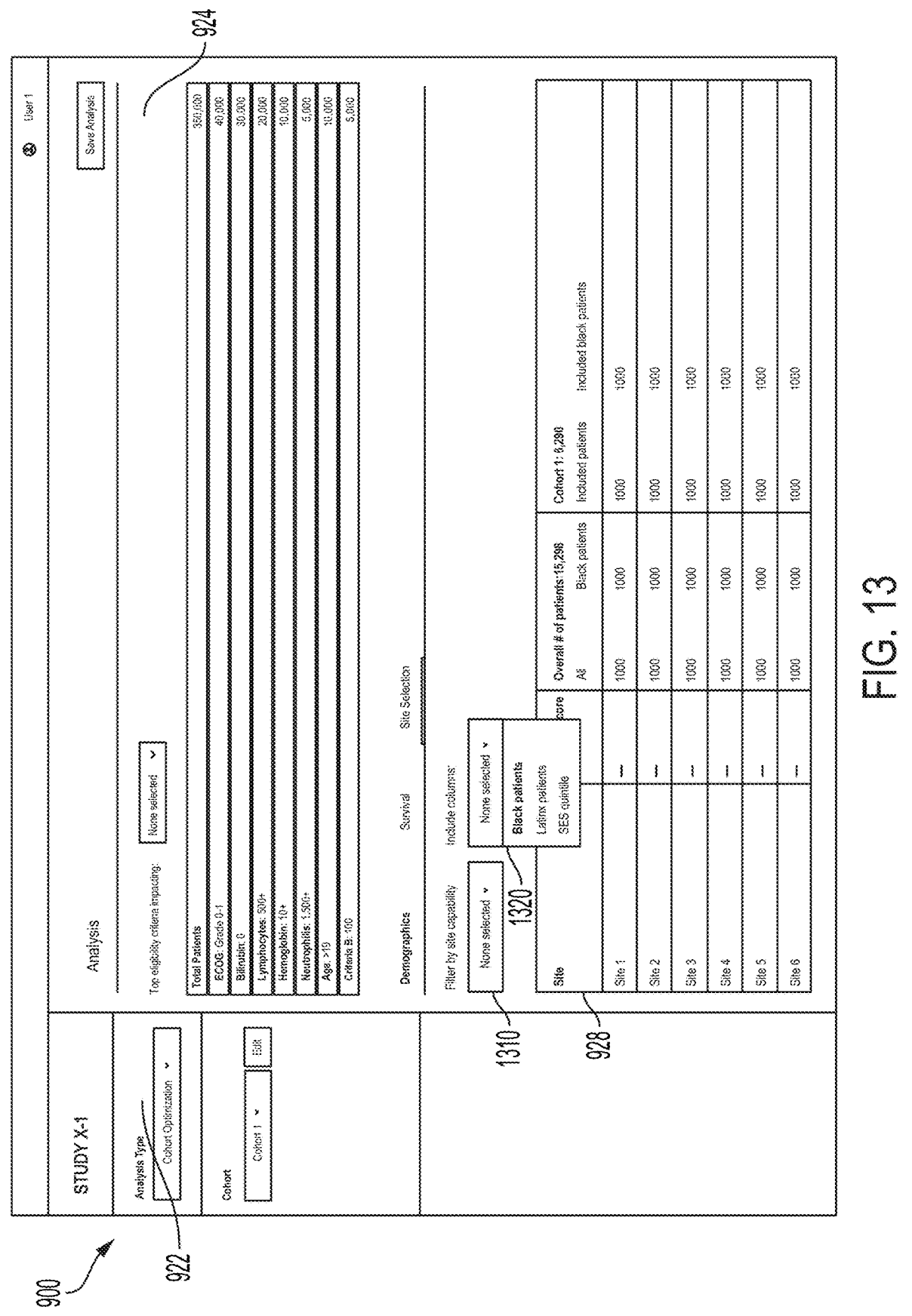

FIG. 13 shows configuration options that can be used to modify the visualization of intervention test site information displayed in the GUI of FIG. 12, according to some embodiments of the technology described herein. As shown in FIG. 13, the GUI element 1310 allows filtering by site capability (e.g., site having phase 1 capabilities, site having phase 2 capabilities, and/or other capabilities) based on user input specifying a site capability. The GUI element 1320 allows addition of columns showing additional information in the table based on input received via GUI element 1320. For instance, selection of "Black patients" via GUI element 1320 causes additional "Black patients" columns to be added to the table 928. The additional columns indicate a total number of black test points at each intervention test site, and a number of black test points included in the intervention test at each intervention test site. As another example, selection of an SES category (e.g., low SES) may cause an additional column(s) to be added to the table 928. The additional column(s) may indicate a total number of test points of the SES category included in the intervention test at each intervention site. In some embodiments, the SES category and test points that belong to the SES category may be determined using socioeconomic variables accessed by the system.

Figure 14:
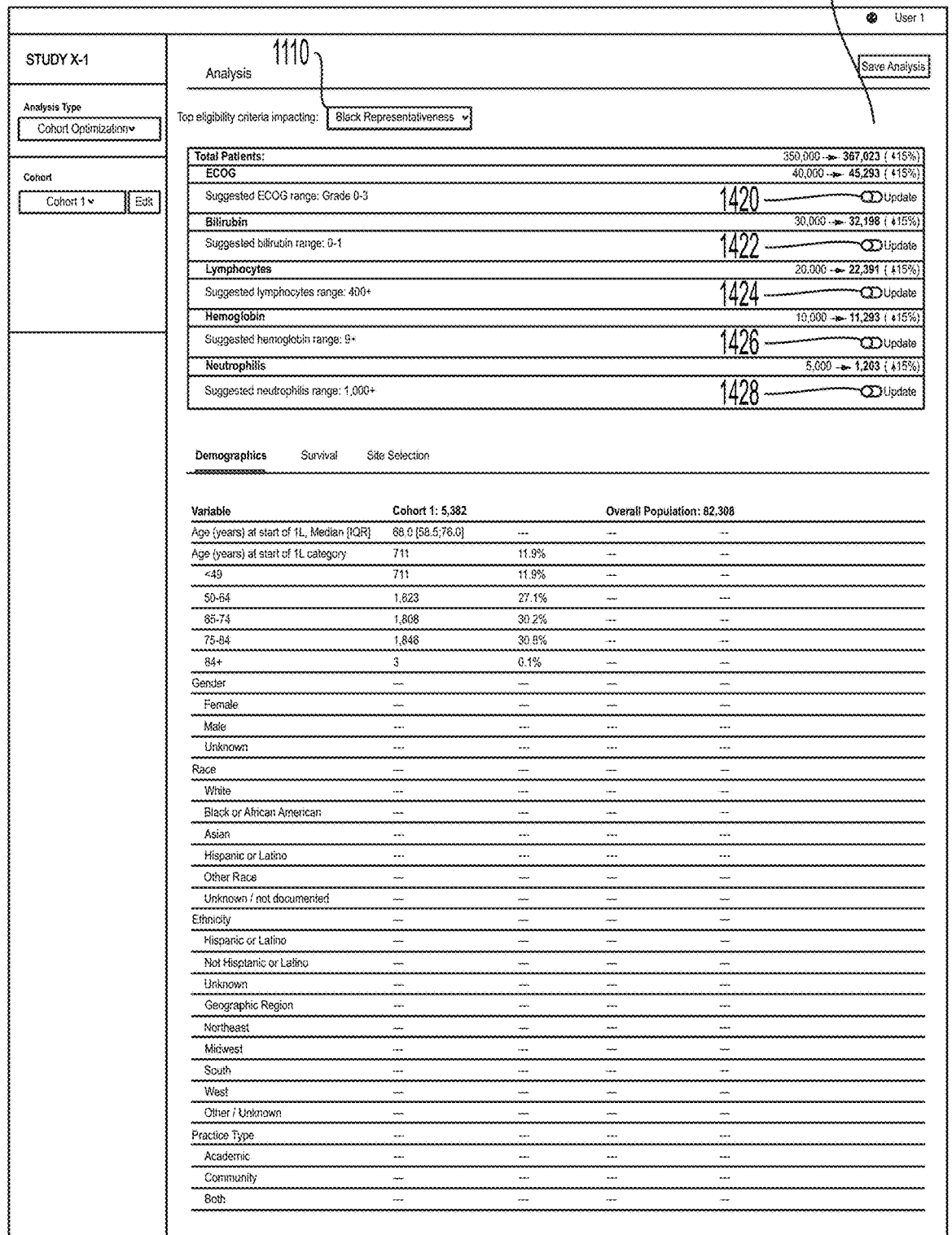
FIG. 14 is an illustrative GUI showing a visualization of demographic information for an intervention test and a control interface that allows modification of control parameters for the intervention test, according to some embodiments of the technology described herein.

In some embodiments, the system may generate a visualization of demographic information for the intervention test. FIG. 14 is the GUI 900 showing a visualization of demographic information for the intervention test, according to some embodiments of the technology described herein. As shown in FIG. 14, a lower area of second GUI portion 924 of GUI 900 includes a table with demographic information. The table includes demographic information about the set of test points included in the intervention test and demographic information about all test points (including those not included in the intervention test). For example, the table may show demographic information for test points diagnosed with DLBCL that are included in the intervention test, and demographic information for all test points diagnosed with DLBCL (including those not included in the intervention test). As shown in FIG. 14, the table displays a number of test points for each of multiple demographic variables (e.g., age ranges, genders, races, ethnicities, geographic regions, and medical practice type). The table further indicates a percentage of test points that meet the demographic variable. For example, the table indicates that there are 711 test points included in the intervention test under the age of 49, and they make up 11.9% of the set of test points included in the intervention test. In some embodiments, demographic distributions may be stratified by time period of date of initial diagnoses (e.g., ≥2019, <2019, etc.) and summarized for test point characteristics of interest (e.g., age at index date, gender, race/ethnicity, geographic region, practice type, year of initial DLBCL diagnosis, number of lines of therapy, group stage at diagnosis, cell of origin at diagnosis, disease subtype, follow-up time from index date to last confirmed activity determined from clinical records, and/or other test point characteristics).

In some embodiments, the system may generate a visualization of socioeconomic characteristics of test points in an intervention test. The system may use SDoH variables to determine the socioeconomic characteristics. The system may generate a graphical and/or tabular depiction of a socioeconomic characteristic of the intervention test using one or more SDoH variables. For example, the system may generate a visualization of an area-level SES index for the intervention test. As another example, the system may generate a visualization of household income, racial segregation, racialized socioeconomic segregation, and/or other variable. In some embodiments, the system may generate a visualization of a geospatial representation of the intervention test. for example, the system may generate a visualization of zip codes and/or tracts represented by the intervention test.

Figure 18:
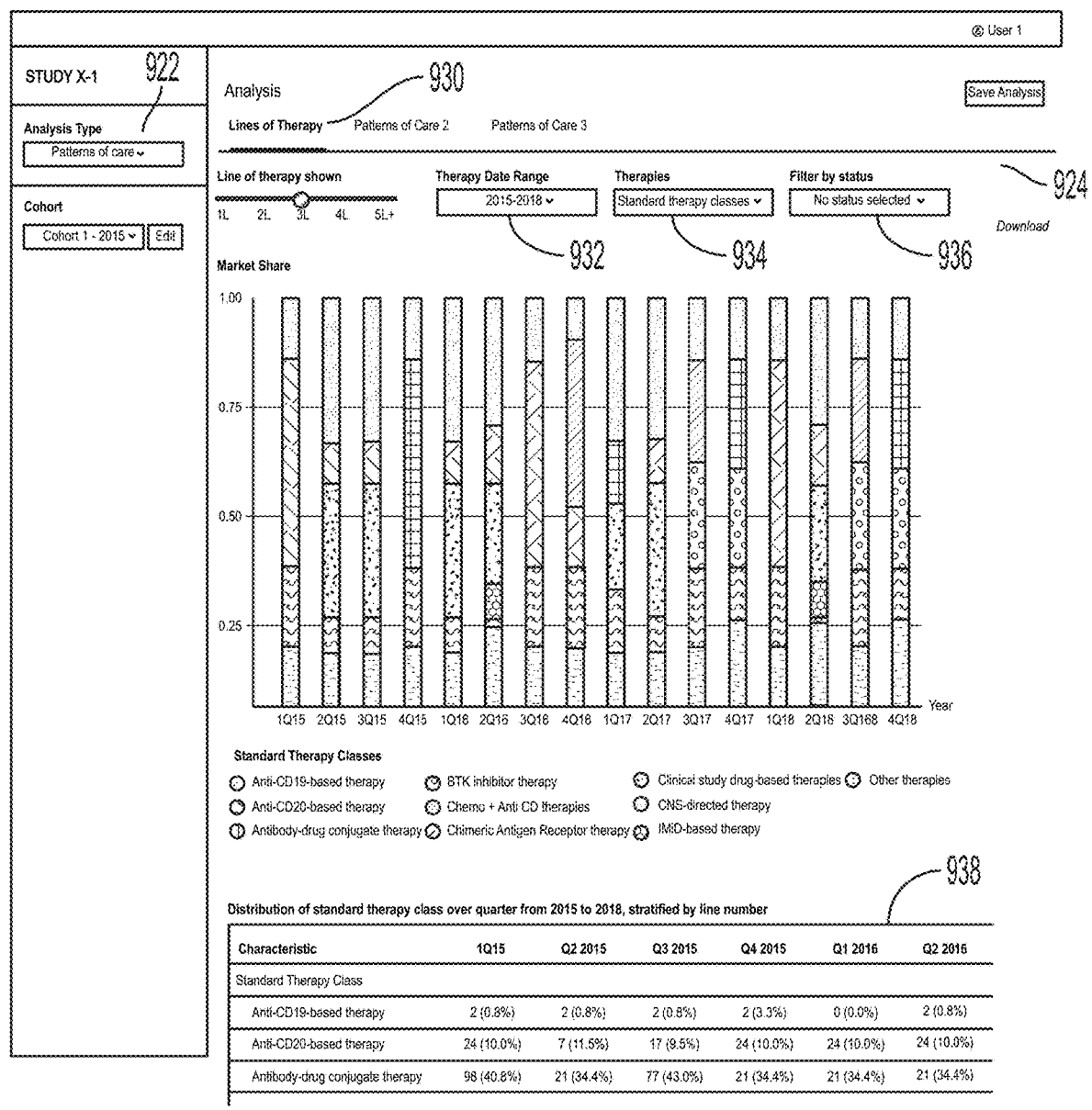
FIG. 18 is an illustrative GUI showing a visualization of pattern of care for a set of test points in an intervention test, according to some embodiments of the technology described herein.

In some embodiments, the system may generate a visualization of pattern of care for the intervention test. FIG. 18 is the GUI 900 showing a visualization of pattern of care for an intervention test, according to some embodiments of the technology described herein. As indicated in the GUI portion 922, the visualization of FIG. 18 may be generated by the system by performing pattern of care control processing. The system may process clinical record data associated with a selected set of test points (e.g., a cohort) to generate a visualization of pattern of care associated with the selected set of test points. Example information regarding patterns of care for test points with a disease (e.g., DLBCL) may include, but not be limited to:

- Describing a distribution of therapy class(es). For example, the distribution of therapy class(es) may be determined by line of therapy—by line number (e.g., first line 1L, second line 2L, third line 3L, etc., and excluding maintenance lines) and/or quarter (e.g., from 2019 to 2022, 2015-2018, etc.). For example, the results may be reported in tabular format and/or graph format for a set of therapy classes.
- Describing a distribution for specific drug names.
- An overall percentage meeting a set of criteria, by line number, and quarterly (e.g., from 2019 to 2022).

The visualization of FIG. 18 includes a visualization of various therapy classes for the selected set of test points. The graph shown in GUI portion 924 shows a market share of different therapy classes during quarters of different years. The GUI portion 924 includes various GUI elements that allow modification of the visualization. For example, the GUI portion 924 in FIG. 18 includes a draggable element 930 that allows a user to adjust a line of therapy for which the visualization is shown. The GUI portion 924 includes an element 932 that allows a user to adjust a date range for which the visualization shows a distribution of therapy classes. The element 934 allows a user to adjust which therapy classes to include in the visualization. The element 936 allows a user to filter by status.

The visualization of FIG. 18 also includes a table 938 showing a distribution of a therapy class (e.g., a standard therapy class). The table 938 shows a number and percentage of test points in each therapy class in each quarter between 2015 and 2018. Another example of a table that may be included in a lower area of second GUI portion 924 of FIG. 18 is shown in FIG. 22. The table describes a distribution of therapy by quarter in the year 2019, stratified by line number of the therapy. In some embodiments, the system may include certain a therapy class in the table when at least one test point has received the therapy in the time period. For example, a therapy in the custom therapy class may only appear in tables when at least one test point has received the therapy in the given time period & line.

Figure 19:
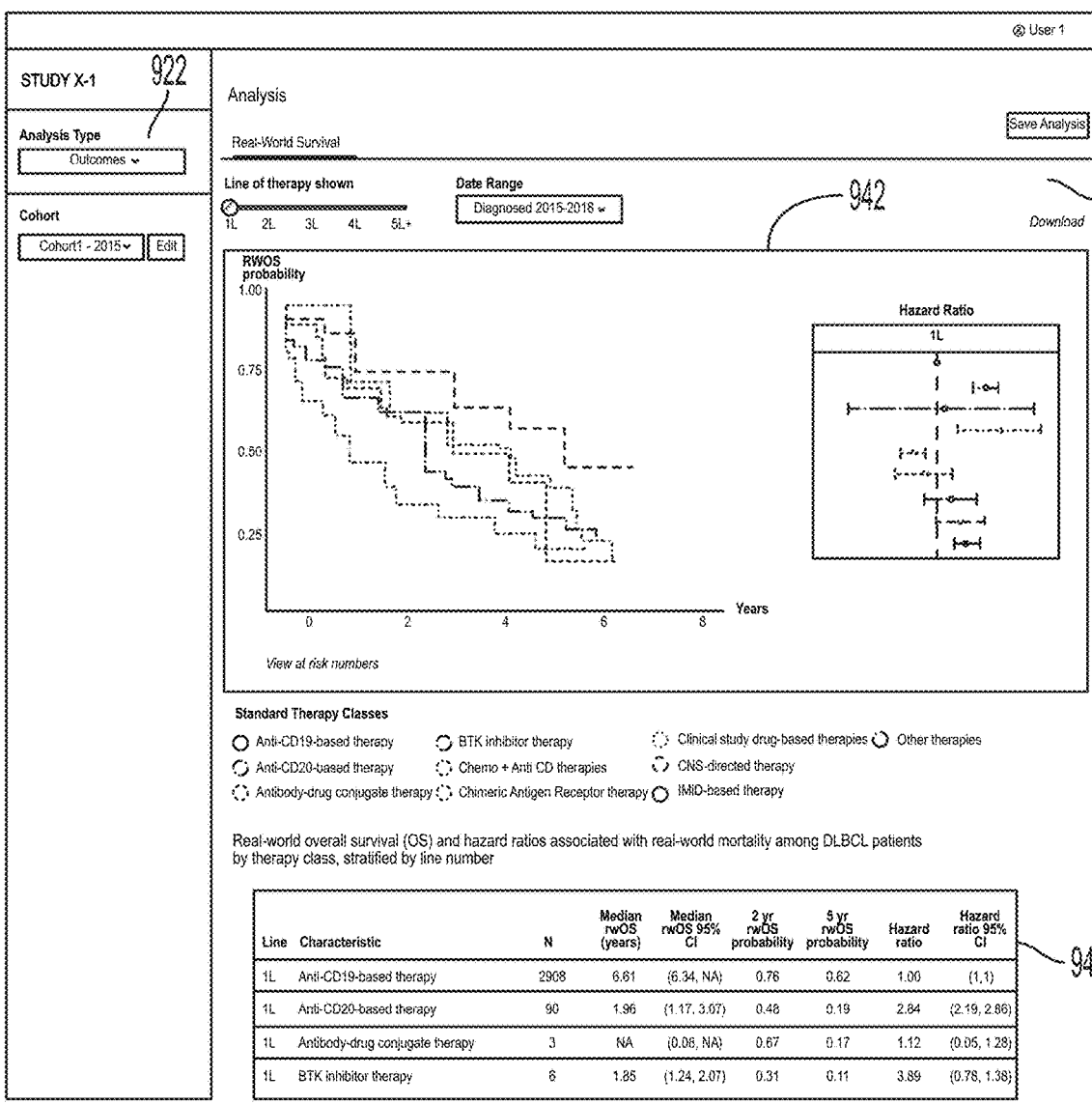
FIG. 19 is an illustrative GUI showing a visualization of an output measure for a set of test points in an intervention test, according to some embodiments of the technology described herein.

In some embodiments, the system may generate a visualization of outcome of different therapy classes for a set of test points in the intervention test. FIG. 19 is the GUI 900 showing a visualization of outcome for a set of test points in an intervention test, according to some embodiments of the technology described herein. As indicated by GUI portion 922, the system may generate the visualization of FIG. 19 by performing control processing to determine real-world outcomes for the set of test points. Real-world outcomes may include precisely defined variables intended to reflect outcomes of interest that are statistically analyzed to address a particular research question. Examples of real-world outcomes include, but are not limited to, real-world overall survival (rwOS) associated with the set of test points, real-world progression-free survival (rwPFS) associated with the set of test points, and real-world time to discontinuation (rwTTD) associated with the set of test points. The system may generate visualization(s) including information regarding the rwOS, rwPFS, and/or rwTTD for the selected cohort. In some embodiments, assessing real-world outcomes may include assessing real-world time to discontinuation (rwTTD) among specifically identified therapy classes or drugs. Such assessment may include conducting unadjusted rwTTD analyses (e.g., using Kaplan-Meier methods, Cox proportional hazard regression models, etc.), stratified by line of therapy and/or a defined set of therapy classes or drugs. Example control processing to assess real-world overall survival (rwOS) for different patterns of care in test points with DLBCL may include, but not be limited to:

- Conducting an unadjusted rwOS analysis on the selected cohort. For example, rwOS control processing may be conducted on two separate cohorts: i) test point lines of therapy initiated from 2015-2018, and 2) test point lines of therapy initiated from 2019 to 2022. Each control processing may be stratified by line of therapy number (excluding maintenance lines)
- Conducting rwOS analyses for the clinically designated therapy classes. Conducting additional rwOS analyses for specific drug names.
- rwOS analyses may be conducted using Kaplan-Meier methods, Cox proportional hazard regression models, and/or other statistical methods.

The visualization of FIG. 19 includes a table 940 shown in lower area of second GUI portion 924 of GUI 900 in FIG. 19. The table 940 shows outcome information for different therapies. The table 940 indicates, for each therapy: a median rwOS, the 95% confidence interval around the median rwOS, 2 year rwOS probability, 5 year rwOS probability, hazard ratio, and the 95% confidence interval for hazard ratio. The visualization of FIG. 19 further includes a graph 942 visualization of outcome information. The graph 942 includes a Kaplan-Meier survival plot along with a forest plot showing the hazard ratio generated based on outputs of cox proportional hazard regression models. The Kaplan-Meier survival plot may include, for each line of therapy/therapy class, a survival curve indicating the probability of survival of test points in the set of test points over time.

In some embodiments, the system may suggest changes to one or more control parameters of an intervention test in order to enable a user to assess the impact of changing the control parameters. For example, the system may suggest changes to control parameters that modify condition(s) for inclusion of test points in the intervention test. The system may dynamically update visualizations to allow a user to assess impacts of changes to control parameter(s). For example, the user may visualize an impact on the number of test points in the set of test points, survival rate or rwOS for the set of test points, distribution across intervention test sites, distribution of therapy classes, and/or other impacts of changes to control parameter(s).

Figure 3:
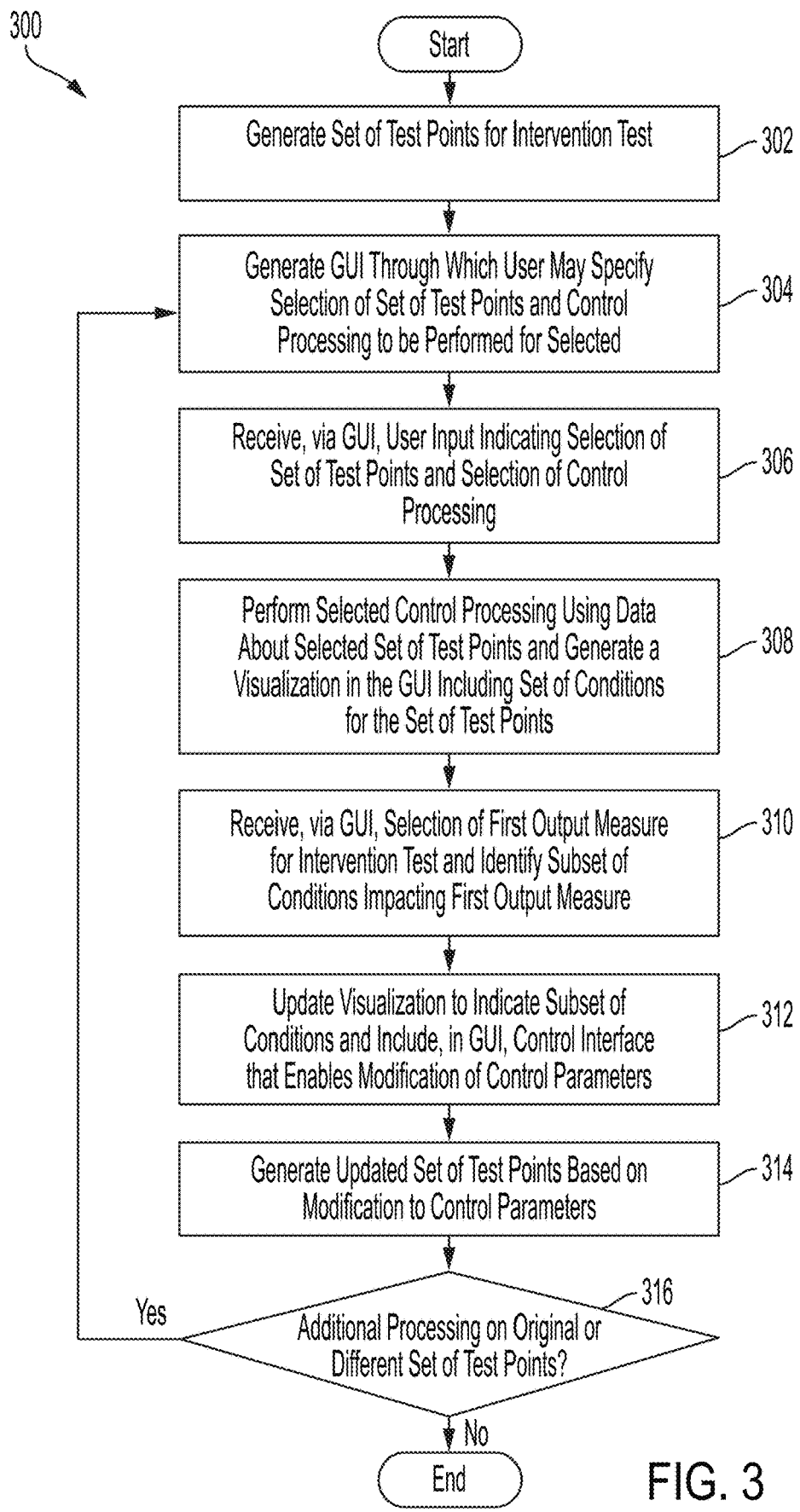
FIG. 3 is a flowchart of an illustrative process for controlling aspects of an intervention test in a graphical intervention test development environment, according to some embodiments of the technology described herein.

FIG. 3 is a flowchart of an illustrative process 300 for controlling aspects of an intervention test in a graphical intervention test development environment, according to some embodiments of the technology described herein. Process 300 may be performed by any suitable computing device. For example, process 300 may be performed by the graphical intervention test development system 110 described herein with reference to FIGS. 1A-1D.

Process 300 begins at act 302, where the system generates a set of test points for an intervention test. The system may generate the set of test points as performed at act 202 of process 200 described herein with reference to FIG. 2.

Next, process 300 proceeds to act 304, where the system generates a GUI through which a user may specify a set of test points and control processing to be performed for the set of test points to generate a visualization. For example, the system may generate the GUI 900 described herein with reference to FIG. 9 including GUI element 902 for specification of an analysis type and a GUI element 904 for specification of a cohort.

Process 300 proceeds to act 306, where the system receives, via the GUI, user input indicating selection of a set of test points (e.g., a cohort) for an intervention test and a selection of control processing (e.g., analysis type) to be performed for the selected set of test points. For example, the system may receive, via the GUI 900 shown in FIG. 9, user input indicating a selection of "Cohort 1" via GUI element 904 and a selection of "Cohort Optimization" control processing via GUI element 902.

Next, process 300 proceeds to act 308, where the system performs the selected control processing for the set of test points and generates a visualization in the GUI. The visualization includes a set of conditions (e.g., eligibility criteria) for inclusion in the intervention test that produced the selected set of test points (e.g., a cohort). For example, the system may generate the visualization 1105 shown in FIG. 11. The visualization 1105 includes the set of eligibility criteria 1140 and for each eligibility criterion, information indicating a number of test points in the cohort that satisfy the eligibility criterion. In the example of FIG. 11, the set of eligibility criteria 1140 includes ECOG status, bilirubin level, lymphocytes level, hemoglobin level, neutrophils, age, and/or other criteria.

In some embodiments, the visualization may indicate information about numbers of test points in the set of test points that satisfy the set of conditions. For example, the visualization 1105 may indicate the total number of test points (e.g., 350,000) in cohort 1 that satisfy the eligibility criteria 1440. The visualization 1105 also includes information indicating a number of test points in cohort 1 that satisfy each eligibility criterion. For example, the number of test points that satisfy the ECOG status criterion is indicated as 40,000, the number of test points that satisfy the bilirubin level criterion is indicated as 30,000, the number of test points that satisfy the lymphocytes level criterion is indicated as 20,000, the number of test points that satisfy the hemoglobin level criterion is indicated as 10,000, the number of test points that satisfy the neutrophils level criterion is indicated as 5,000, the number of test points that satisfy the age criterion is indicated as 10,000, and the number of test points that satisfy the "Criteria B" criterion is indicated as 5,000.

In some embodiments, the GUI may include a GUI element through which a user can indicate an output measure for the intervention test to evaluate. For example, the visualization 1105 of FIG. 11 includes GUI element 1110 configured to receive input indicating a selection of an output measure for the intervention test (e.g., representativeness, absolute test point count, and survival).

In some embodiments, the GUI may provide multiple different visualizations. For example, the GUI may allow a user to navigate between different types of visualizations obtained from performing the control processing. In the example of FIG. 9, the GUI portion 924 includes selectable tabs labeled "Demographics", "Survival", and "Site Selection." Selection of each tab may cause the system to render a respective visualization in the GUI. For example, selection of the "Demographics" tab causes the system to render a visualization of demographic information associated with cohort 1 in the GUI (e.g., as shown in FIG. 14), selection of "Survival" tab causes the system to render a visualization of the overall survival rate or rwOS of cohort 1 in the GUI (e.g., as shown in FIG. 11), and selection of "Site Selection" tab causes the system to render a visualization of site-related information associated with cohort 1 in the GUI (e.g., as shown in FIG. 12). In some embodiments, the system may process clinical record data associated with test points in the cohort 1 and/or information regarding test points enrolled at one or more sites to generate visualizations.

Next, process 300 proceeds to act 310, where the system receives, through the GUI, the selection of a first output measure for the intervention test and identifies a subset of the set of conditions impacting the first output measure. Example output measures for an intervention test include black representativeness, Hispanic/Latino counts, Hispanic/Latino representativeness, low socioeconomic counts, low socioeconomic representativeness, concentration of non-English speakers, and/or concentration of non-car ownership. As illustrated in the example of FIG. 14, input indicating a selection of the output measure for the intervention test may be received via GUI element 1110. In some embodiments, the system may identify the subset of eligibility criteria using one or more rules. For example, the system may use guidelines set by the FDA, National Cancer Institute (NCI), and/or another entity. In some embodiments, the system may identify the subset of eligibility criteria using statistical methods described herein. In the example of FIG. 14, the system identified a subset of eligibility criteria impacting black representativeness to include ECOG status, bilirubin level, lymphocytes level, hemoglobin level, and neutrophils. As another example, the system may identify a subset of eligibility criteria impacting a socioeconomic group (e.g., low SES).

In some embodiments, the system may use clinical data points (e.g., obtained from clinical record data associated with the set of test points) to identify and suggest changes to one or more control parameters for the intervention test that control the subset of conditions. In some embodiments, the system may use various data science approaches, such as rules-based approaches, simulations, machine learning, and/or other techniques to suggest changes to one or more conditions in a way that increases the eligible test point population. For example, the system may use data about the set of test points to generate a set of feature values and provide the set of feature values as input to a trained machine learning model to obtain output indicating a change to one or more eligibility criteria. In some embodiments, the system may identify a change without negatively impacting endpoints such as hazard ratio. In some embodiments, the system may identify a change while affecting endpoints such as hazard ratio (e.g., in order to improve representativeness of certain subsets of the population).

As an illustrative example, an intervention test may initially have a requirement that estimated glomerular filtration rate (eGFR) is greater than a threshold of 60 mL/min/1.73 m$^2$ for a test point to be included in the intervention test. The system may suggest changing the threshold to 30 mL/min/1.73 m$^2$. The system may determine to suggest the change by: (1) identifying the change in the threshold; (2) processing clinical data points to determine an effect on an output measure; and (3) determining to suggest the change when it is determined that the change has a desired effect on the output measure. To illustrate, the system may determine that the change in the threshold increases the number of test points included in the intervention test from 950 to 1300 and that it increases black representativeness (e.g., by increasing the eligible Black population). The system may thus suggest changes in one or more control parameters that control the eGFR threshold for inclusion of test points in the intervention test. As another example, the system may determine a change in the threshold to improve low socioeconomic representativeness of the test points included in the intervention test.

Next, process 300 proceeds to act 312, where the system updates the visualization to indicate the identified subset of conditions and include, in the GUI, a control interface that enables modification to control parameters that control the subset of conditions. For example, the system may update the visualization 1105 to display a subset of the eligibility criteria 1140 shown in FIG. 11. The updated visualization is shown in FIG. 14. As shown in FIG. 14, the subset of eligibility displayed include ECOG status, bilirubin level, lymphocytes level, hemoglobin level, and neutrophils but not age and criteria B.

In the example of FIG. 14, the system updated GUI 900 to include a control interface that allows modification of control parameters. The control interface may include GUI elements (e.g., toggles, check boxes, input text field, and/or other elements) that allow modification to the control parameters. In the example of FIG. 14, the control interface includes GUI elements 1420, 1422, 1424, 1426, 1428, where each GUI element is configured to receive input indicating a change to the respective eligibility criterion. GUI element 1420 allows the user to modify a control parameter to change an ECOG range for inclusion of test points to grade 0-3. GUI element 1422 allows the user to modify a control parameter to change a Bilirubin range for inclusion of test points to 0-1. GUI element 1424 allows the user to modify a control parameter to change a lymphocytes range for inclusion of test points to 400 or more. GUI element 1426 allows the user to modify a control parameter to change a hemoglobin range for inclusion of test points to 9 or more. GUI element 1428 allows the user to modify a control parameter to change neutrophils range for inclusion of test points to 1,000 or more. As shown in FIG. 14, the system further includes, in the control interface, an indication of the change in number of test points that would result in modification of a control parameter. For example, modifying the toggle of GUI element 1420 to change the ECOG range condition results in the number of test points meeting the ECOG range condition to increase from 40,000 test points to 45,293 test points and an associated percentage increase.

Figure 15:
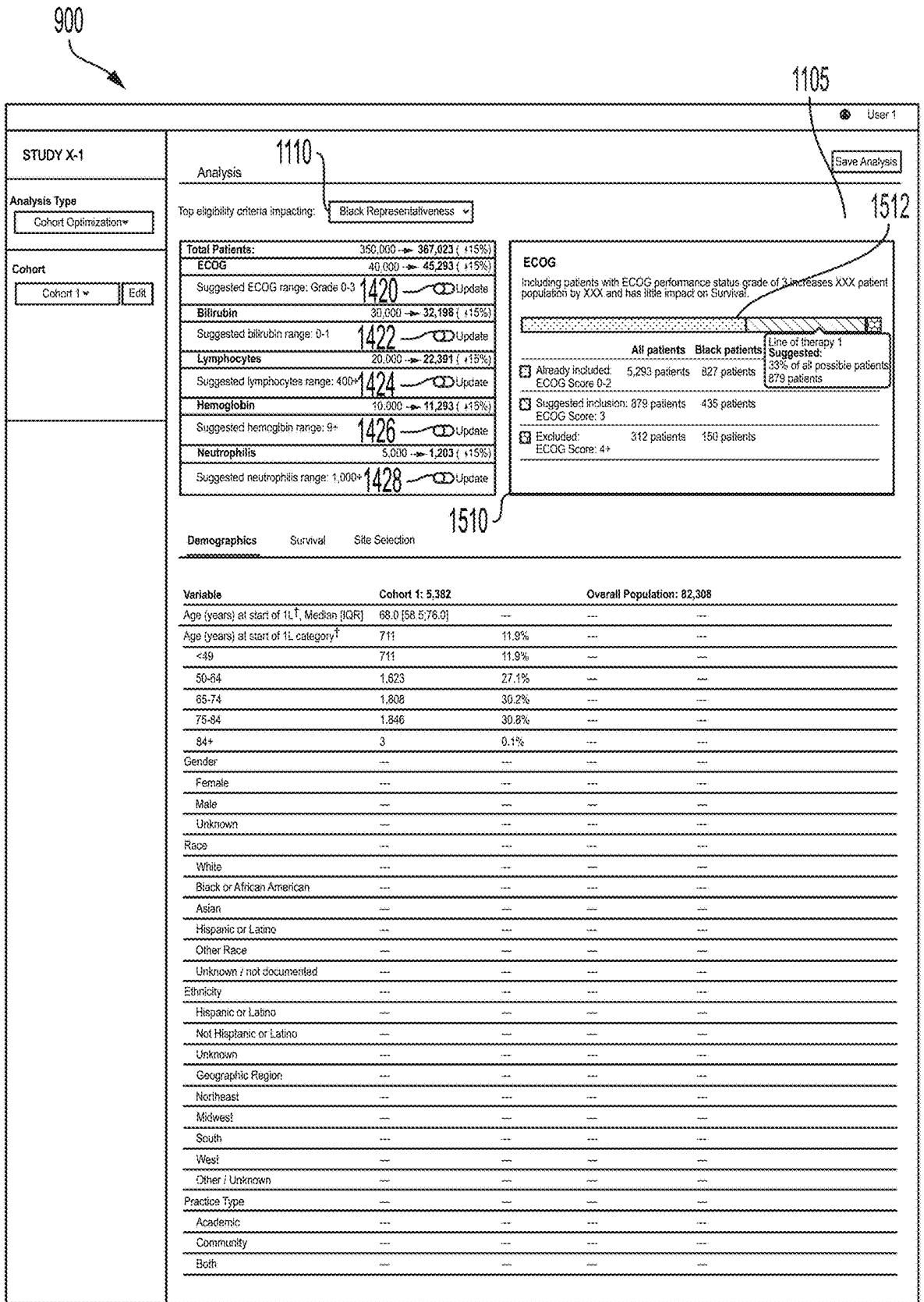
FIG. 15 is an illustrative GUI showing an updated visualization of FIG. 14 that shows additional information about a control parameter that can be modified through a control interface, according to some embodiments of the technology described herein.

In some embodiments, the system may update the visualization to display more information about a particular control parameter in the control interface. For example, the system may display more information about a condition affected by modification of the control parameter. FIG. 15 is the GUI 900 showing additional information about a control parameter that can be modified in the control interface of FIG. 14, according to some embodiments of the technology described herein. In the example of FIG. 15, the system has updated the visualization to include a detailed view 1510 of information about the selected ECOG range control parameter. Input indicating a selection of a particular eligibility criterion may be received by clicking on the name (e.g., ECOG) or a location within the vicinity of the displayed name of the eligibility criterion. The view 1510 includes a visualization of suggested changes for the condition controlled by the control parameter. The detailed view 1510 includes text explaining the impact of modifying the control parameter (e.g., including test points with an ECOG status grade of 3), information regarding the number of test points with a particular ECOG status/range (e.g., ECOG score 0-2) that are already included in the cohort 1, information regarding the number of test points with a particular ECOG status/range (e.g., ECOG score 3) that were not previously included in cohort 1 and would be included after the modification to the control parameter, and the information regarding the number of test points with a particular ECOG status/range (e.g., ECOG score 4 and higher) that are excluded from cohort 1. In some embodiments, the detailed view 1502 may also include a visualization 1512 of a fraction of total test points in each category (already included, suggested inclusion, and excluded). In the example of FIG. 15, the visualization 1512 is a graphical depiction of a fraction of each category of test points.

In some embodiments, the system may include information about the particular output measure selected by the user (e.g., through GUI element 1110 in FIG. 14). In the example of FIG. 15, the system included information in the detailed view 1510 with respect to black representativeness. The view 1510 indicates numbers of black test points with ECOG score 0-2 that are already included in the cohort 1, a number of black test points with ECOG score 3 that were not previously included in cohort 1 and that the system is now suggesting to include in cohort 1, and the number of black test points with ECOG score of 4 or more that are excluded from cohort 1. As another example, the system may include information in the detailed view 1510 with respect to low socioeconomic status representativeness. The view 1510 may indicate numbers of low socioeconomic test points with ECOG score 0-2 that are already included in cohort 1, a number of low socioeconomic test points with ECOG score 3 that were not previously included in cohort 1 and that the system is now suggesting including in cohort 1, and the number of low socioeconomic test points with ECOG score of 4 or more that are excluded from cohort 1.

Figure 16:
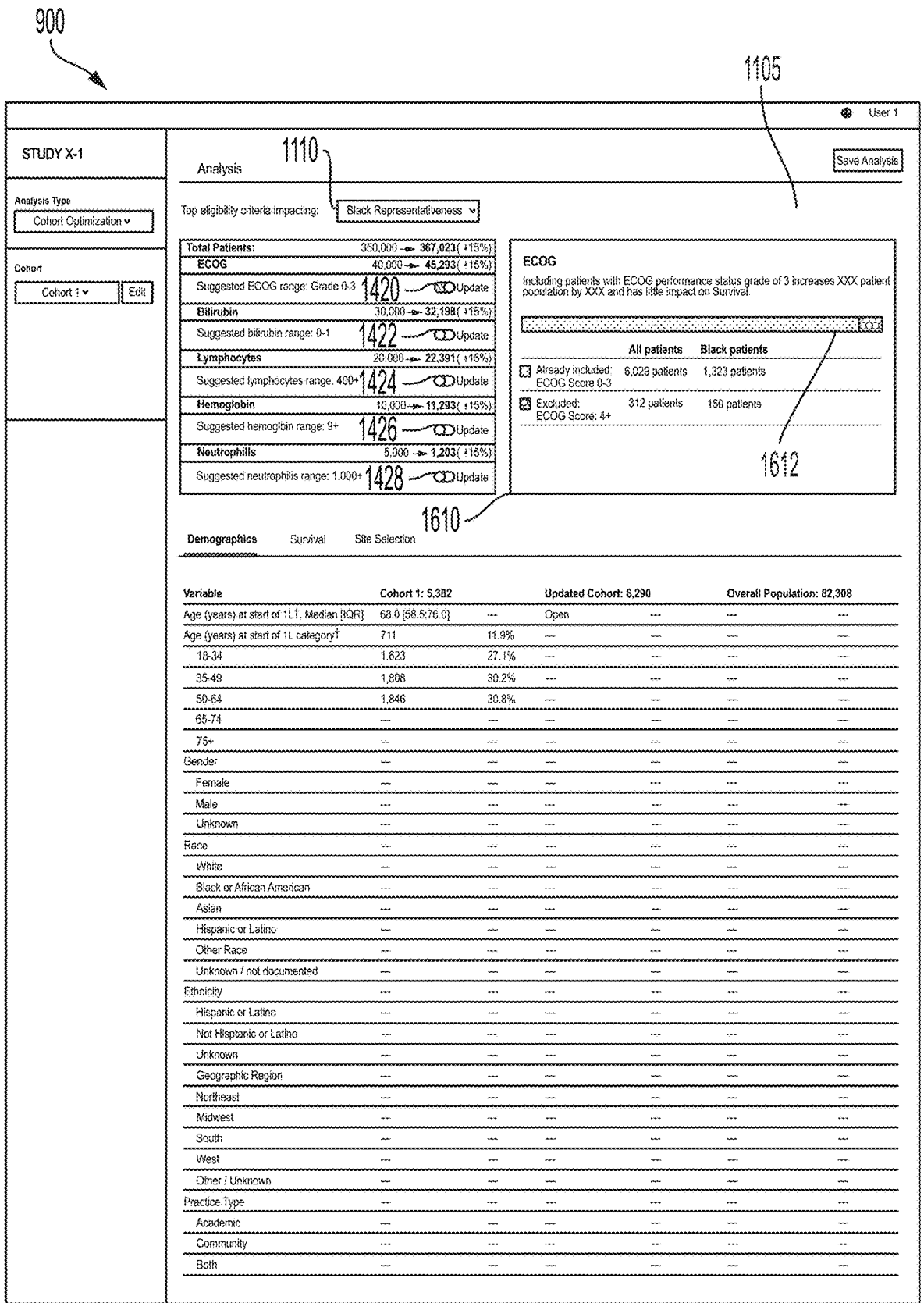
FIG. 16 is an illustrative GUI showing an updated visualization of FIG. 15 after modification of a control parameter, according to some embodiments of the technology described herein.

Continuing with the example of FIG. 15, the system may receive, via GUI element 1420, an input indicating a change to ECOG status. In response to the modification in the control parameter, the system may dynamically update the visualization to obtain the visualization shown in FIG. 16. FIG. 16 shows the GUI of FIG. 15 with an updated visualization generated by the system after modification of the control parameter, according to some embodiments of the technology described herein. As can be seen in FIG. 16, a user toggled the toggle switch 1420 to the right to indicate a change or update to the ECOG status criterion. In response to this user input, the system modified a control parameter indicating the ECOG status criterion for inclusion in the intervention test. The system determines a change to the number of test points in cohort 1 that satisfy the ECOG status criterion after the control parameter modification. This change causes the number of test points in the already included category to increase. The system updates the display at least in part by updating the detailed view 1510 of FIG. 15 to obtain the updated view 1610 of FIG. 16. As can be seen in FIG. 16, the updated view 1610 includes an update to the visualization of information associated with the control parameter. The updated view 1610 includes an updated graphical depiction 1612 of the number of test points that meet the updated condition for inclusion in the intervention test versus the number of test points that do not. The system updated the view 1610 to indicate a number of test points with ECOG score 0-3 which are included in the intervention test, and a number of test points with ECOG score 4 or more which are excluded.

Next, process 300 proceeds to act 314, where the system generates an updated set of test points (e.g., a cohort) for the intervention test based on modification to one or more control parameters (e.g., through a control interface provided by the system). In some embodiments, the system may generate the updated set of test points responsive to selection (e.g., toggling) of one or more the GUI elements (e.g., GUI elements 1420, 1422, 1424, 1426, and 1428 described herein with reference to FIG. 14). The system may generate the updated set of test points based on the selections. For example, the system may generate the updated set of test points by adding test points that now meet an updated set of conditions generated as a result of the modification to the control parameter(s).

Figure 17:
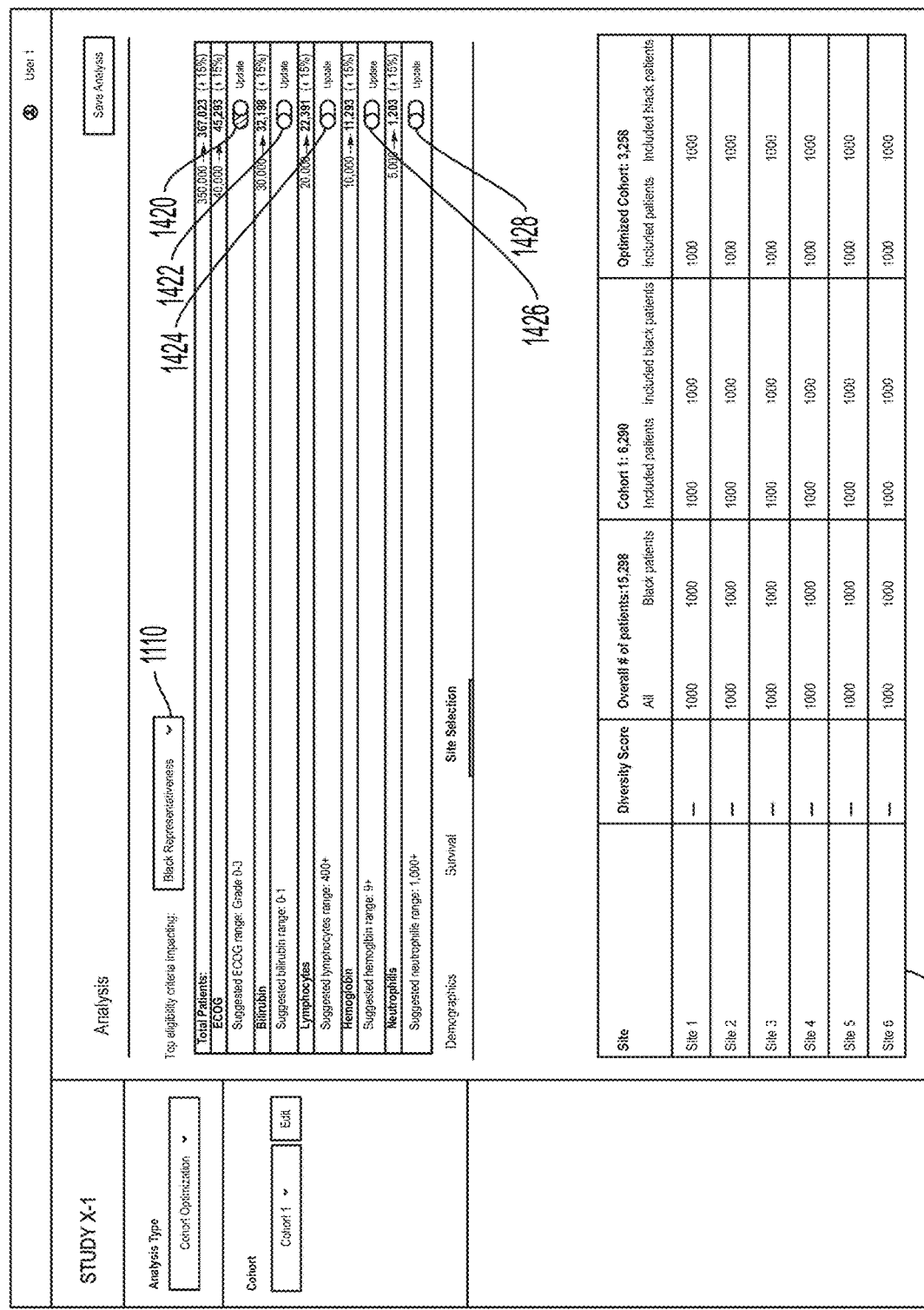
FIG. 17 is an illustrative GUI showing an updated visualization of site selection for an intervention test after modification of a control parameter, according to some embodiments of the technology described herein.

In some embodiments, the system may update a visualization as part of generating the updated set of test points. For example, as illustrated in FIGS. 15-16 the system updated visualization 1105 to update the detailed view 1510 to obtain view 1610. In some embodiments, the system may generate and display a visualization including information regarding the updated set of test points. The information regarding the updated cohort may include demographic information regarding the updated set of test points (e.g., as shown in FIG. 16), overall survival of the updated set of test points, and site information indicating a distribution of the number of test points in the updated set of test points across one or more intervention test sites. FIG. 17 is the GUI 900 showing an updated visualization of site selection for an intervention test after modification of a control parameter, according to some embodiments of the technology described herein. The updated visualization includes a table indicating test points across various intervention test sites updated relative to the table of FIG. 13. The table 942 includes a section indicating a distribution of the original set of test points across the intervention sites, and an additional section indicating a distribution of the updated set of test points across the intervention sites. Accordingly, the system provides a visualization of the update to the distribution of test points across the intervention sites based on the modification to the control parameter.

In some embodiments, the system may update the visualization when a user closes out of a detailed view showing information about a control parameter. In some embodiments, when the user closes out the detailed and/or updated views, the system may adjust dimensions in the GUI (e.g., dimensions of the control interface and/or other portions of the visualization 1105). The system may adjust dimensions in the GUI such that the control interface returns to its original dimensions (e.g., as shown in FIG. 14).

Accordingly, the system allows for graphically designing an intervention test in a graphical development environment. The system performs processing using test point data to generate visualizations of aspects of the intervention test. The system further provides an interface to adjust control parameters and graphically view results of control parameter modifications on the intervention test (e.g., on output measures of the intervention test).

In some embodiments, selection of the "Save Analysis" button in various GUIs (for example, in GUIs shown in FIGS. 14-17 or other GUIs) may cause the system to generate GUI 2000, where the saved result of performing control processing (e.g., an analysis) is added to the profile view of the intervention test. As shown in FIG. 20, a cohort optimization control analysis is added to the profile view of the intervention test. In some embodiments, saving a control processing may include saving the control processing type, the set of test points (e.g., the updated set of test points), and any control parameter modifications.

Next, process 300 proceeds to act 316, the system determines whether input is received to perform additional control processing on the original set of test points or a different set of test points. If the system receives input indicating additional control processing is to be performed, then process 300 proceeds to block 304. For example, selection of the "View dashboard" button in GUI 2000 of FIG. 20 may indicate that additional control processing is to be performed and trigger generation and display of GUI 900 of FIG. 9, where the process may loop back to act 304. If the system does not receive input indicating that additional processing is to be performed, then process 300 ends.

FIG. 23 is an illustrative GUI 2300 showing manipulation of a GUI element 2302 to modify a control parameter controlling a condition for inclusion of test points in an intervention test, according to some embodiments of the technology described herein. The modification of the control parameter changes the ECOG range required for test points to be included in the intervention test. GUI 2300 also includes a visualization of demographic information for an updated cohort created as a result of the change. The "New trial eligible cohort" indicates a number of test points in the cohort after modification to the control parameter (e.g., using associated GUI element 2302).

As can be seen in FIG. 23, GUI 2300 includes an "Enrollment Projections" tab in addition to the "Demographics", "Survival", and "Site Selection" tabs.

Figure 24:
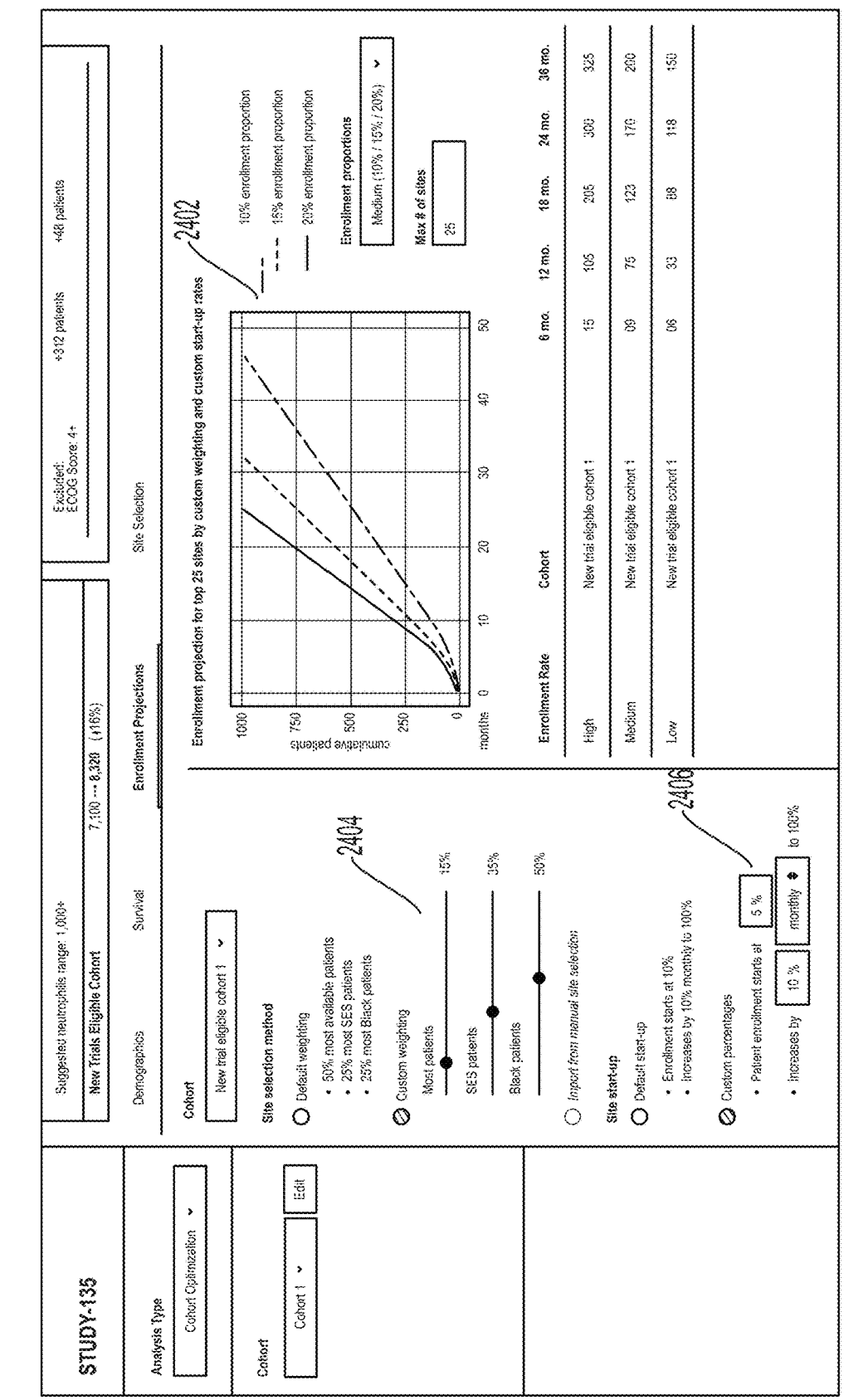
FIG. 24 is an illustrative GUI showing a visualization of enrollment projections for an intervention test, according to some embodiments of the technology described herein.

Selection of the enrollment projections tab causes the system to render a visualization shown in GUI 2400 of FIG. 24. FIG. 24 is an illustrative GUI 2400 showing a visualization 2402 of enrollment projections for an intervention test, according to some embodiments of the technology described herein. The visualization 2402 displayed in GUI 2400 may indicate estimated enrollment rate for the updated set of test points across multiple sites over time. The GUI 2400 further includes various GUI elements to manipulate control parameters for the intervention test. The GUI 2400 includes element 2404 that allows a user to modify a weighting of different categories of test points (e.g., patients) using a draggable GUI element. The GUI element 2406 provides various fields to adjust control parameters of patient enrollment start percentage, increase in enrollment, and frequency of increase in enrollment. The system may dynamically update the visualization 2402 responsive to control parameter modifications using GUI elements 2404, 2406.

Figure 25:
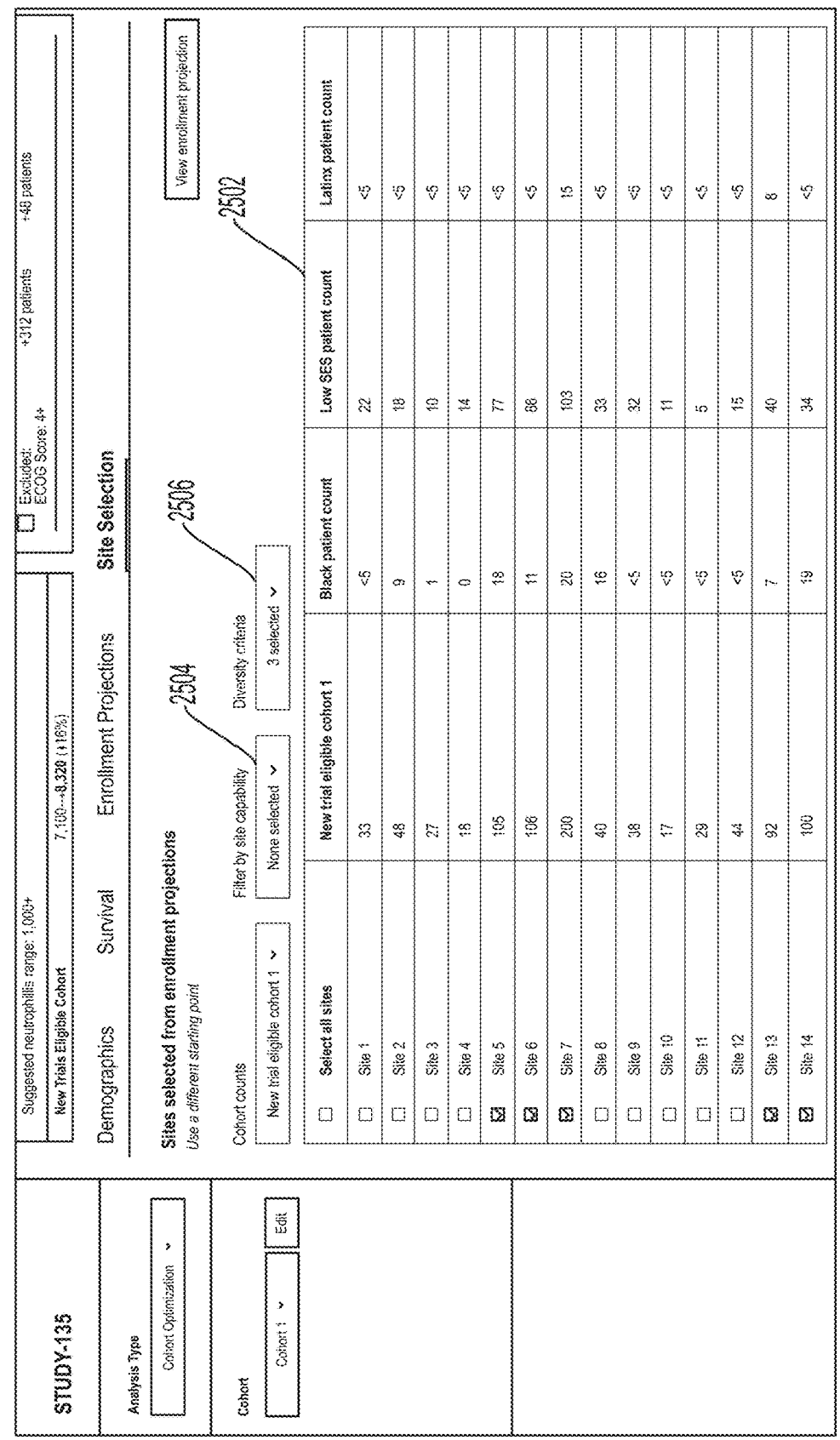
FIG. 25 is an illustrative GUI showing a visualization of candidate distribution across intervention sites, according to some embodiments of the technology described herein.

Selection of the site selection tab may cause the system to render the visualization shown in GUI 2500 of FIG. 25. FIG. 25 is an illustrative GUI 2500 showing a visualization 2502 of test point distribution across intervention sites, according to some embodiments of the technology described herein. GUI 2500 of FIG. 25 shows that a set of sites are automatically selected for enrollment of the updated set of test points (i.e., "New trial eligible cohort 1") based on the enrollment projections information. In some embodiments, site selection for an intervention test may include filtering or adjusting sites based on optimizing for a particular outcome, such as black representativeness or black test point enrollment. In some embodiments, selection of the "View enrollment projection" button may cause the system to render the visualization of enrollment projections of FIG. 25. The GUI 2500 includes a menu 2504 from which a user can select a site capability filter. The system may update the visualization 2504 in response to selection of a site capability filter. The GUI 2500 also includes a diversity criteria menu 2506 that allows selection of diversity criteria for the intervention test. In the example of FIG. 25, the selected diversity criteria are Black patient count, low SES patient count, and Latinx patient count.

In some embodiments, while the enrollment projection control processing is shown as part of the cohort optimization control processing, it will be appreciated that enrollment projection control processing may be a standalone control processing that may be included as one of the selectable options for control processing type, for example, via selection of an option presented using GUI element 134.

In some embodiments, the system may generate one or more visualizations of aggregated data. One such visualization is a visualization of stratification of test points with respect to a characteristic, such as line of therapy or therapy class. Examples of aggregations may include counts, percentages, averages, medians, and/or other aggregations. Examples of visualizations may include stacked bar plot/graph, Sankey diagrams, line charts, and/or other visualizations. In some embodiments, aggregates may provide information, such as, about test points that received first line of therapy for DLBCL in the first quarter of 2019, a number of test points received anti-cd19-based therapy; a total number of test points receiving first line therapy for DLBCL in the first quarter of 2019; a number of the test points receiving first line therapy for DLBCL in the first quarter 2019, and a percentage of test points received anti-cd19-based therapy.

Figure 26:
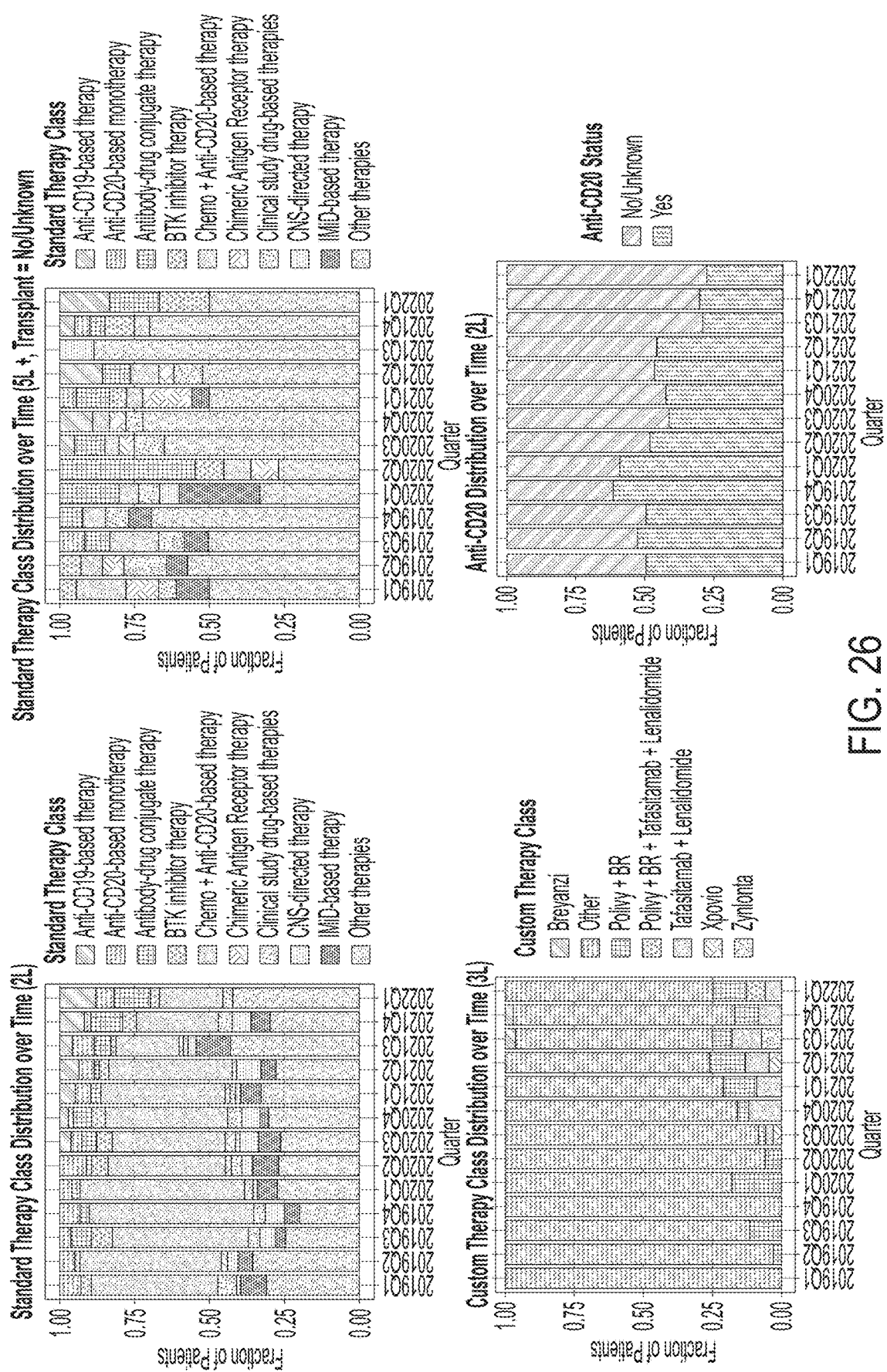
FIG. 26 shows illustrative visualizations of test point distribution among various therapy classes, according to some embodiments of the technology described herein.

FIG. 26 shows illustrative visualizations of test point distribution among various therapy classes, according to some embodiments of the technology described herein. The system may render the visualizations of FIG. 26 in example GUIs described herein. Each of the graphs shown in FIG. 26 is a stratified bar graph indicating a distribution of test points (e.g., patients) across various different types of therapies during each quarter of a time period. The graphs provide visualizations of test point distribution across different therapies in different therapy classes.

In some embodiments, the system may perform statistical analyses (e.g., epidemiologic statistical analyses) that may be stratified over any test point characteristic, such as line of therapy or therapy class, and generate associated visualizations. The system may display stratified visualizations via one or more GUIs described herein.

Figure 27A:
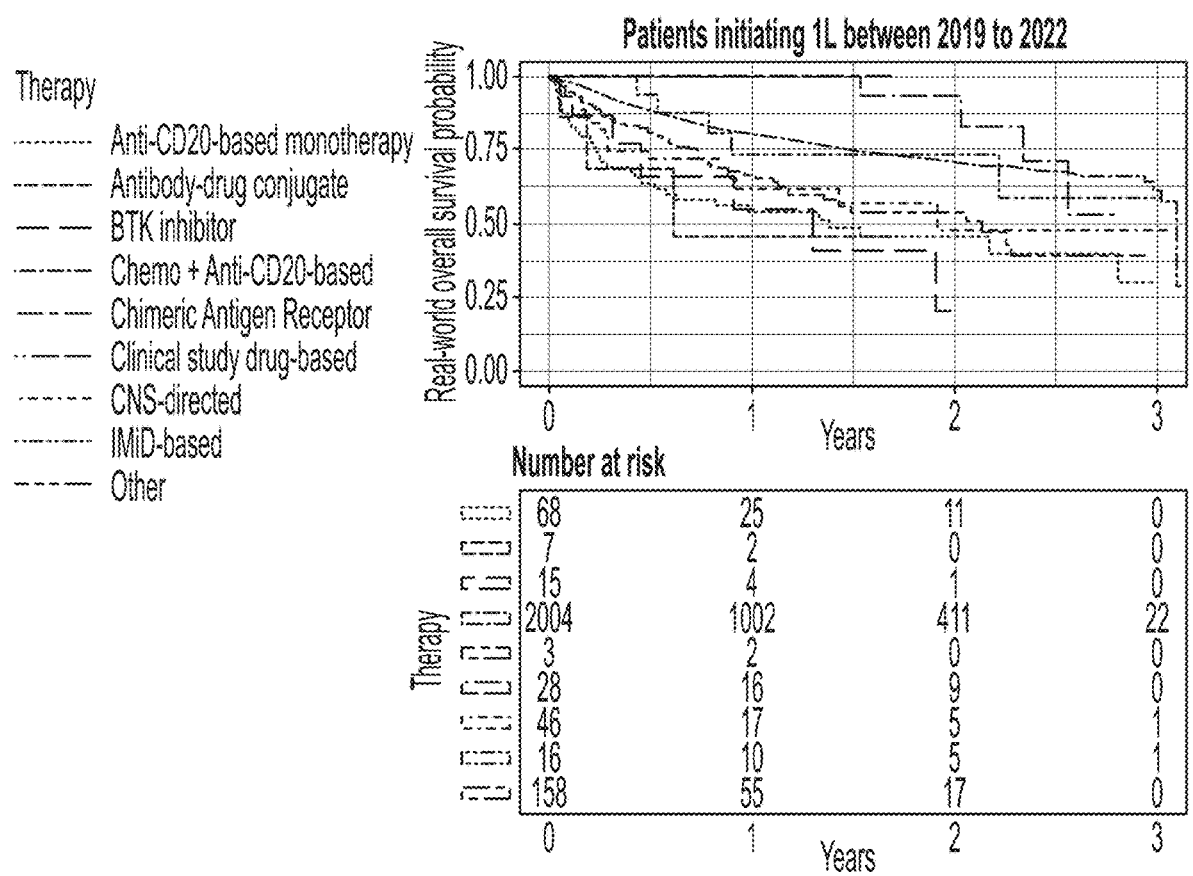
FIG. 27A shows an illustrative visualization of survival for a set of test points, according to some embodiments of the technology described herein.

In some embodiment, the system may perform control processing using data about test points to determine information about survival outcomes. FIG. 27A shows an illustrative visualization of survival for a set of test points, according to some embodiments of the technology described herein. The top graph in FIG. 27A is a visualization of real-world overall survival probability for various different therapies over a period of approximately 3 years. The bottom graph in FIG. 27A is a visualization of a number of test points at risk for each therapy in each year of a time period.

Figure 27B:
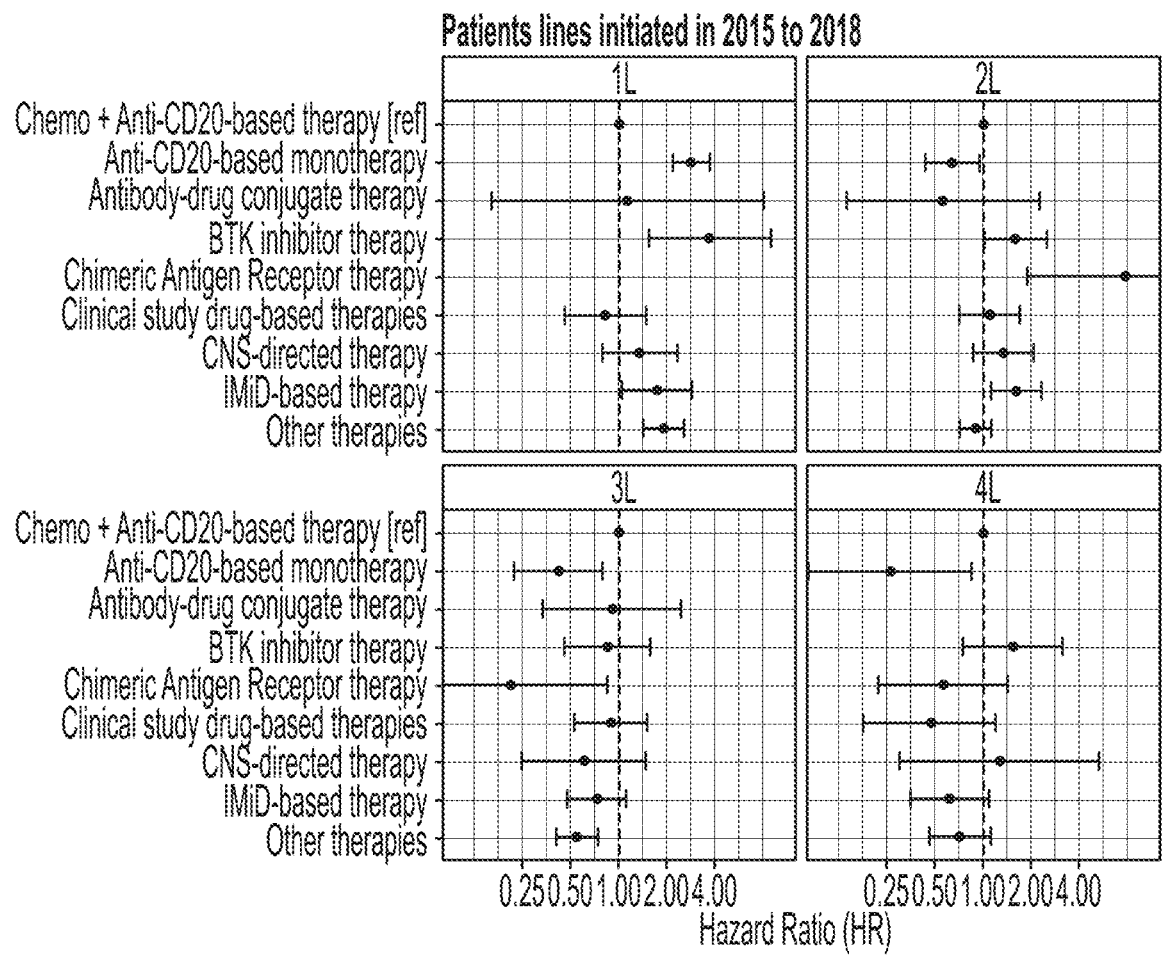
FIG. 27B shows a visualization of hazard ratios for different lines of various therapies, according to some embodiments of the technology described herein.

In some embodiments, the system perform control processing using data about test points to determine hazard ratio for various different therapies. FIG. 27B shows a visualization of hazard ratios for different lines of various therapies, according to some embodiments of the technology described herein. FIG. 27B includes hazard ratio graphs for lines of therapy initiated between the time period 2015 to 2018.

In some embodiments, the system may use data about test points to perform control processing to determine representativeness of a population. FIG. 28 shows an example visualization of representativeness of a set of test points, according to some embodiments of the technology described herein. FIG. 28 includes a table shown representativeness of various different factors (A, B, C). The table shows a US cancer population percentage with the factor, a percentage of test points in the data with the factor, and a percentage of test points included in an intervention test (e.g., a trial) with the factor. The table further includes columns indicating metrics (e.g., scores) of representativeness of available test point data, and of test points included in the intervention test.

In some embodiments, the system may perform control processing to determine metrics about intervention sites. FIG. 29 shows an example visualization of metrics for various intervention sites, according to some embodiments of the technology described herein. FIG. 29 includes a table with various metrics (e.g., Metric 1, Metric 2) for each intervention site (e.g., A, B, C) and a weighted score for each intervention site.

In some embodiments, the system may further model impact of changes (e.g., eligibility criteria, assessment schedule, sites, etc.) on the above types of control processing. The system may provide a control interface through which control parameter(s) may be modified and resulting effects of a modification are reflected by changes in visualizations. Accordingly, a user may attain a visual depiction of modification to the control parameter(s) (e.g., a change in representativeness or other output measure).

Example control processing and visualizations are described herein for illustrative purposes. Some embodiments may perform control processing in addition to and/or instead of example control processing described herein. Some embodiments may generate visualizations in addition to and/or instead of example visualizations described herein. Further, while a certain number and/or types of sets of test points, control processing, and GUI elements are shown and described herein, any suitable number and/or types of sets of test points, control processing, and GUI elements may be used as aspects of the disclosure provided herein are not limited in this respect.

Also, while various examples in this disclosure are described with respect to a particular disease DLBCL, it will be appreciated that aspects described herein may be used for and applied to other disease areas as aspects of the disclosure provided herein are not limited in this respect. It will also be appreciated that one or more test point characteristics, eligibility criteria, and/or parameters included in various GUIs may differ to account for a particular disease area.

Figure 21:
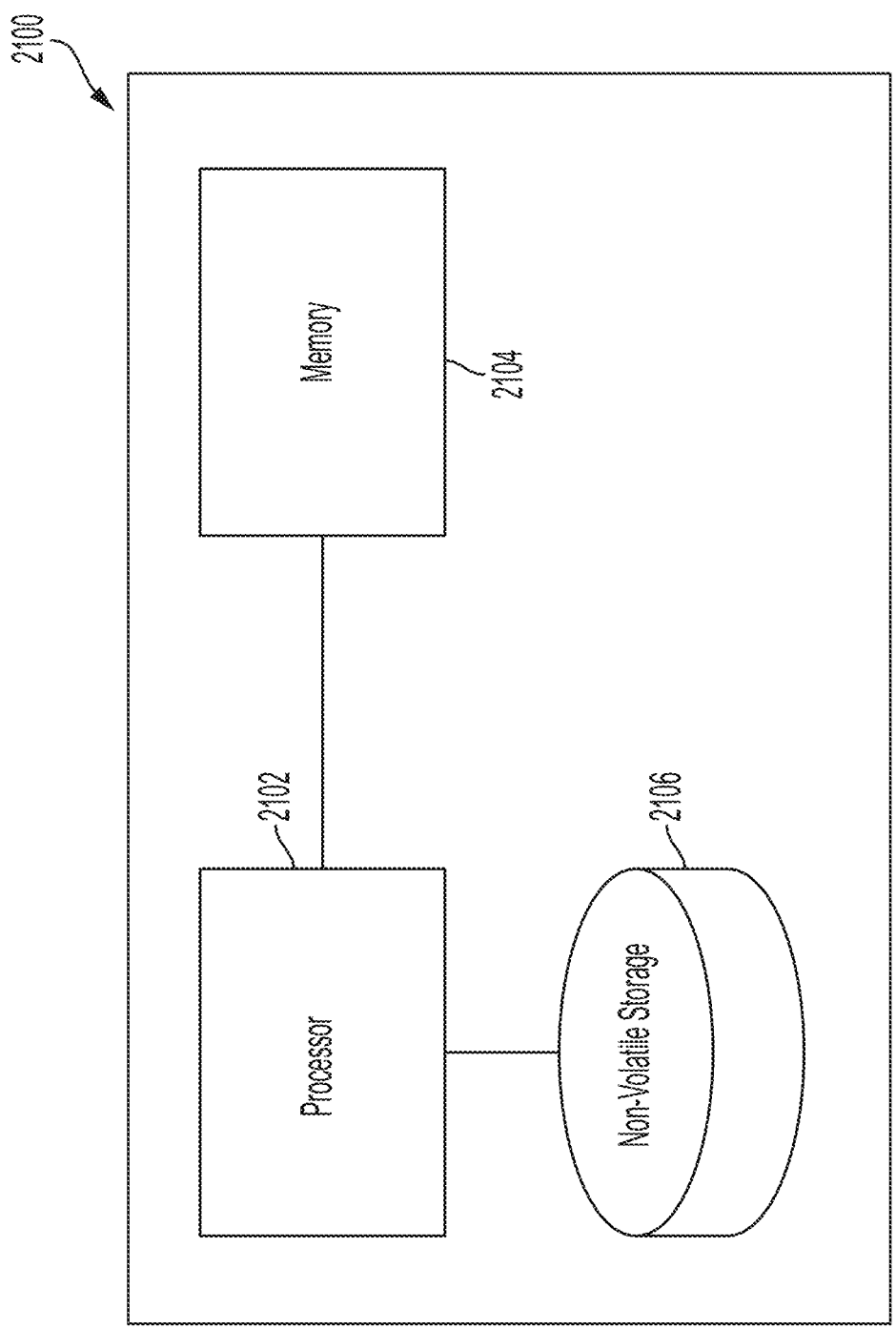
FIG. 21 is a diagram of an illustrative computing system that may be used in implementing some embodiments of the technology described herein.

FIG. 21 shows an illustrative implementation of a computing device 2100 that may be used in connection with any of the embodiments of the disclosure provided herein. The computing device 2100 may include one or more computer hardware processors 2102 and one or more articles of manufacture that comprise non-transitory computer-readable storage media (e.g., memory 2104 and one or more non-volatile storage devices 2106). The processor 2102(*s*) may control writing data to and reading data from the memory 2104 and the non-volatile storage device(s) 2106 in any suitable manner. To perform any of the functionality described herein, the processor(s) 2102 may execute one or more processor-executable instructions stored in one or more non-transitory computer-readable storage media (e.g., the memory 2104), which may serve as non-transitory computer-readable storage media storing processor-executable instructions for execution by the processor(s) 2102.

Having thus described several aspects of at least one embodiment of the technology described herein, it is to be appreciated that various alterations, modifications, and improvements will readily occur to those skilled in the art.

Such alterations, modifications, and improvements are intended to be part of this disclosure, and are intended to be within the spirit and scope of disclosure. Further, though advantages of the technology described herein are indicated, it should be appreciated that not every embodiment of the technology described herein will include every described advantage. Some embodiments may not implement any features described as advantageous herein and in some instances one or more of the described features may be implemented to achieve further embodiments. Accordingly, the foregoing description and drawings are by way of example only.

The above-described embodiments of the technology described herein can be implemented in any of numerous ways. For example, the embodiments may be implemented using hardware, software or a combination thereof. When implemented in software, the software code can be executed on any suitable processor or collection of processors, whether provided in a single computer or distributed among multiple computers. Such processors may be implemented as integrated circuits, with one or more processors in an integrated circuit component, including commercially available integrated circuit components known in the art by names such as CPU chips, GPU chips, microprocessor, microcontroller, or co-processor. Alternatively, a processor may be implemented in custom circuitry, such as an ASIC, or semicustom circuitry resulting from configuring a programmable logic device. As yet a further alternative, a processor may be a portion of a larger circuit or semiconductor device, whether commercially available, semicustom or custom. As a specific example, some commercially available microprocessors have multiple cores such that one or a subset of those cores may constitute a processor. However, a processor may be implemented using circuitry in any suitable format.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, aspects of the technology described herein may be embodied as a computer readable storage medium (or multiple computer readable media) (e.g., a computer memory, one or more floppy discs, compact discs (CD), optical discs, digital video disks (DVD), magnetic tapes, flash memories, circuit configurations in Field Programmable Gate Arrays or other semiconductor devices, or other tangible computer storage medium) encoded with one or more programs that, when executed on one or more computers or other processors, perform methods that implement the various embodiments described above. As is apparent from the foregoing examples, a computer readable storage medium may retain information for a sufficient time to provide computer-executable instructions in a non-transitory form. Such a computer readable storage medium or media can be transportable, such that the program or programs stored thereon can be loaded onto one or more different computers or other processors to implement various aspects of the technology as described above. As used herein, the term "computer-readable storage medium" encompasses only a non-transitory computer-readable medium that can be considered to be a manufacture (i.e., article of manufacture) or a machine. Alternatively or additionally, aspects of the technology described herein may be embodied as a computer readable medium other than a computer-readable storage medium, such as a propagating signal.

The terms "program" or "software" are used herein in a generic sense to refer to any type of computer code or set of computer-executable instructions that can be employed to program a computer or other processor to implement various aspects of the technology as described above. Additionally, it should be appreciated that according to one aspect of this embodiment, one or more computer programs that when executed perform methods of the technology described herein need not reside on a single computer or processor, but may be distributed in a modular fashion amongst a number of different computers or processors to implement various aspects of the technology described herein.

Computer-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the technology described herein may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the technology described herein may be embodied as one or more processes, of which examples have been provided. The acts performed as part of any of the methods may be ordered in any suitable way. Accordingly, embodiments may be constructed in which acts are performed in an order different than illustrated, which may include performing some acts simultaneously, even though shown as sequential acts in illustrative embodiments.

Further, some actions are described as taken by a "user". It should be appreciated that a "user" need not be a single individual, and that in some embodiments, actions attributable to a "user" may be performed by a team of individuals and/or an individual in combination with computer-assisted tools or other mechanisms.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed is:

1. A graphical intervention test development system comprising:
   a processor;
   a non-transitory computer-readable storage medium storing instructions that, when executed by the processor, cause the processor to execute a plurality of components of the graphical intervention development system, the plurality of components comprising:
      an intervention data module communicatively coupled to a database storing data about potential test points as values of fields, the intervention data module configured to:
         access a set of control parameters associated with an intervention test, the set of control parameters indicating a set of conditions for inclusion in the intervention test;
         access, from the database, data about a set of test points that meet the set of conditions indicated by the set of control parameters; and
         for each condition of the set of conditions, determine, using the data about the set of test points, a number of the set of test points that meet the condition;
      a graphical processing module configured to generate a graphical intervention test development environment, the graphical intervention test development environment comprising a graphical user interface (GUI), the graphical processing module configured to:
         receive, through the GUI, input indicating selection of the set of test points and selection of first control processing to be performed using the data about the set of test points; and
         receive, through the GUI, input indicating selection of second control processing to be performed using the data about the set of test points, the second control processing comprising determining survival associated with the set of test points; and
      an intervention test control module configured to:
         execute the first control processing using the data about the set of test points, wherein execution of the first control processing using the data causes the graphical processing module to render, in the GUI, a first visualization of the intervention test, the first visualization comprising:
            a plurality of graphical elements each representing a respective one of at least some the set of conditions and indicating a determined number of the set of test points that meet the condition;
         receive, through the GUI, input indicating an output measure of the intervention test, wherein the output measure comprises at least one of representativeness of a group, absolute test point count, and survival;
         identify one or more of the set of control parameters that impact the output measure of the intervention test; and
         execute the second control processing using the data about the set of test points, wherein execution of the second control processing using the data causes the graphical processing module to render, in the GUI, a second visualization indicating the survival associated with the set of test points;
      wherein the graphical processing module is further configured to update the first visualization by including, in the first visualization, a control interface configured to allow user modification of the one or more control parameters that impact the output measure.

2. The system of claim 1, wherein:
   the intervention control module is further configured to determine an impact of a modification to the one or more control parameters to a number of test points that would meet the set of conditions after the modification; and
   the graphical processing module is further configured to include, in the first visualization, a graphical indication of the determined impact of the modification to the one or more control parameters to the number of test points that would meet the set of conditions after the modification.

3. The system of claim 2, wherein the graphics processing module is further configured to:
   receive, through the control interface, input indicating a first modification to a first control parameter of the one or more control parameters that changes the set of conditions for inclusion in the intervention test.

4. The system of claim 3, wherein the graphical processing module is further configured to:
   generate an updated set of test points that meet the updated set of conditions in response to the first modification to the first control parameter to obtain an updated set of test points.

5. The system of claim 4, wherein the graphical processing module is further configured to:
   render, in the GUI, a visualization of the intervention test using data about the updated set of test points.

6. The system of claim 5, wherein the visualization of the intervention test indicates at least one of demographic distribution, survival rate, and/or distribution of test points across multiple intervention sites for the updated set of test points.

7. The system of claim 1, wherein the graphical processing module is further configured to:
generate, in the GUI, a GUI portion configured to receive input indicating the set of control parameters, the set of control parameters including at least one control parameter indicating a disease shared by the set of test points.

8. The system of claim 1, wherein:
the graphical processing module is further configured to receive, through the GUI, input indicating selection of third control processing to be performed using the data about the set of test points, the third control processing comprising determining patterns of intervention for the set of test points; and
the intervention test control module is further configured to execute the third control processing using the data, wherein execution of the third control processing using the data causes the graphical processing module to render, in the GUI, a third visualization indicating the patterns of intervention for the set of test points.

9. A method of providing a graphical intervention test development environment for use in computer-based design of an intervention test, the method comprising:
using a processor to perform:
accessing a set of control parameters associated with the intervention test, the set of control parameters indicating a set of conditions for inclusion in the intervention test;
accessing, from a database storing data about potential test points as values of fields, data about a set of test points that meet the set of conditions indicated by the set of control parameters;
determining, for each condition of the set of conditions, using the data about the set of test points, a number of the set of test points that meet the condition;
generating the graphical intervention test development environment, the graphical intervention test development environment comprising a GUI;
receiving, through the GUI, input indicating selection of the set of test points and selection of first control processing to be performed using the data about the set of test points;
executing the first control processing using the data about the set of test points;
rendering, in response to execution of the first control processing, a first visualization of the intervention test, the first visualization comprising:
a plurality of graphical elements each representing a respective one of at least some of the set of conditions and indicating a determined number of the set of test points that meet the condition;
receiving, through the GUI, input indicating an output measure of the intervention test;
identifying one or more of the set of control parameters that impact the output measure of the intervention test, wherein the output measure comprises at least one of a target of representativeness, absolute test point count, and survival;
updating the first visualization by including, in the first visualization, a control interface configured to allow user modification of the one or more control parameters that impact the output measure;
receiving, through the GUI, input indicating selection of second control processing to be performed using the data about the set of test points, the second control processing comprising determining survival associated with the set of test points;
executing the second control processing using the data; and
rendering, in the GUI in response to executing the second control processing, a second visualization indicating the survival associated with the set of test points.

10. The method of claim 9, further comprising:
determining an impact of modification to the one or more control parameters to a number of test points that would meet the set of conditions after the modification; and
including, in the first visualization, a graphical indication of the determined impact of the modification to the one or more control parameters to the number of test points that would meet the set of conditions after the modification.

11. The method of claim 10, further comprising receiving, through the control interface, input indicating a first modification to a first control parameter of the one or more control parameters that changes the set of conditions for inclusion in the intervention test.

12. The method of claim 11, further comprising generating an updated set of test points that meet the updated set of conditions in response to the first modification to the first control parameter to obtain an updated set of test points.

13. The method of claim 12, further comprising rendering, in the GUI, a visualization of the intervention test using data about the updated set of test points.

14. The method of claim 9, further comprising generating, in the GUI, a GUI portion configured to receive input indicating the set of control parameters, the set of control parameters including at least one control parameter indicating a disease shared by the set of test points.

15. The method of claim 9, further comprising:
receiving, through the GUI, input indicating selection of third control processing to be performed using the data about the set of test points, the third control processing comprising determining patterns of intervention for the set of test points;
executing the third control processing using the data; and
rendering, in the GUI in response to executing the third control processing, a third visualization indicating the patterns of intervention for the set of test points.

16. A non-transitory computer-readable medium storing instructions that, when executed by a processor, cause the processor to perform a method of providing a graphical intervention test development environment for use in computer-based design of an intervention test, the method comprising:
accessing a set of control parameters associated with the intervention test, the set of control parameters indicating a set of conditions for inclusion in the intervention test;
accessing, from a database storing data about potential test points as values of fields, data about a set of test points that meet the set of conditions indicated by the set of control parameters;
determining, for each condition of the set of conditions, using the data about the set of test points, a number of the set of test points that meet the condition;
generating the graphical intervention test development environment, the graphical intervention test development environment comprising a GUI;

receiving, through the GUI, input indicating selection of the set of test points and selection of first control processing to be performed using the data about the set of test points;

executing the first control processing using the data about the set of test points;

rendering, in response to execution of the first control processing, a first visualization of the intervention test, the first visualization comprising:
 a plurality of graphical elements each representing a respective one of at least some of the set of conditions and indicating a determined number of the set of test points that meet the condition;

receiving, through the GUI, input indicating an output measure of the intervention test;

identifying one or more of the set of control parameters that impact the output measure of the intervention test, wherein the output measure comprises at least one of a target of representativeness, absolute test point count, and survival;

updating the first visualization by including, in the first visualization, a control interface configured to allow user modification of the one or more control parameters that impact the output measure;

receiving, through the GUI, input indicating selection of second control processing to be performed using the data about the set of test points, the second control processing comprising determining survival associated with the set of test points;

executing the second control processing using the data; and rendering, in the GUI in response to executing the second control processing, a visualization indicating the survival associated with the set of test points.

* * * * *